US007858581B2

(12) United States Patent
Cunningham et al.

(10) Patent No.: US 7,858,581 B2
(45) Date of Patent: Dec. 28, 2010

(54) PMMA BINDING PEPTIDES AND METHODS OF USE

(75) Inventors: Scott D. Cunningham, Chadds Ford, PA (US); David J. Lowe, Wilmington, DE (US); John P. O'Brien, Oxford, PA (US); Hong Wang, Kennett Square, PA (US); Antoinette E. Wilkins, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 724 days.

(21) Appl. No.: 11/607,732

(22) Filed: Dec. 1, 2006

(65) Prior Publication Data

US 2007/0265431 A1    Nov. 15, 2007

Related U.S. Application Data

(60) Provisional application No. 60/750,548, filed on Dec. 15, 2005.

(51) Int. Cl.
*A61K 38/02* (2006.01)
*C10M 145/14* (2006.01)

(52) U.S. Cl. .................. 514/3.2; 530/421; 508/469

(58) Field of Classification Search .................. None
See application file for complete search history.

(56) References Cited

U.S. PATENT DOCUMENTS

| | | | |
|---|---|---|---|
| 4,416,873 A | 11/1983 | Puchalski et al. | |
| 4,482,537 A | 11/1984 | El-Menshawy et al. | |
| 5,192,332 A | 3/1993 | Lang et al. | |
| 5,223,409 A | 6/1993 | Ladner et al. | |
| 5,403,484 A | 4/1995 | Ladner et al. | |
| 5,425,937 A | 6/1995 | Uchiwa et al. | |
| 5,449,754 A | 9/1995 | Nishioka | |
| 5,480,971 A | 1/1996 | Houghten et al. | |
| 5,490,980 A | 2/1996 | Richardson et al. | |
| 5,571,698 A | 11/1996 | Ladner et al. | |
| 5,585,275 A | 12/1996 | Hudson et al. | |
| 5,597,386 A | 1/1997 | Igarashi et al. | |
| 5,639,603 A | 6/1997 | Dower et al. | |
| 5,837,500 A | 11/1998 | Ladner et al. | |
| 6,013,250 A | 1/2000 | Cannell et al. | |
| 6,267,957 B1 | 7/2001 | Green et al. | |
| 6,280,747 B1 | 8/2001 | Philippe et al. | |
| 6,344,443 B1 | 2/2002 | Liu et al. | |
| 6,537,330 B1 | 3/2003 | Hoeffkes et al. | |
| 6,620,419 B1 | 9/2003 | Lintner | |
| 2002/0098524 A1 | 7/2002 | Murray et al. | |
| 2003/0152976 A1 | 8/2003 | Janssen et al. | |
| 2003/0185870 A1 | 10/2003 | Grinstaff et al. | |
| 2005/0054752 A1 | 3/2005 | O'Brien et al. | |
| 2007/0065387 A1 * | 3/2007 | Beck et al. | 424/70.13 |

FOREIGN PATENT DOCUMENTS

| | | |
|---|---|---|
| EP | 0570583 A1 | 11/1993 |
| EP | 0634161 A1 | 1/1995 |
| JP | 02311412 A | 12/1990 |
| JP | 06065049 A | 3/1994 |
| JP | 08104614 A | 4/1996 |
| JP | 09003100 A | 1/1997 |
| JP | 2002363026 | 12/2002 |
| JP | 2004-331630 | 11/2004 |
| WO | WO 00/48558 | 8/2000 |
| WO | WO 01/07009 A1 | 2/2001 |
| WO | WO 01/45652 A1 | 6/2001 |
| WO | WO 01/79479 A2 | 10/2001 |
| WO | WO 02/065134 A2 | 8/2002 |
| WO | WO 03/031477 A1 | 4/2003 |
| WO | WO 03/102020 A2 | 12/2003 |
| WO | WO 2004/000257 A2 | 12/2003 |
| WO | WO 2004/048399 A2 | 6/2004 |
| WO | WO 2004/069211 A2 | 8/2004 |

OTHER PUBLICATIONS

S. G. Dixit et al., Combinatorial Chemistry—Principles and Practices, Journal of Scientific & Industrial Research, vol. 57:173-183, 1998.
Ronald H. Hoess, Protein Design and Phage Display, Chem. Rev., vol. 101:3205-3218, 2001.
Todd C. Holmes, Novel peptide-based biomaterial scaffolds for tissue engineering, TRENDS in Biotechnology, vol. 20(1):16-21, 2002.
Sandra R. Whaley et al., Selection of peptides with semiconductor binding specificity for directed nanocrystal assembly, Nature, vol. 405:665-668, 2000.
Marc S. Reisch, Ingredients makers take lessons from biotechnology to mastermind the latest in personal care, C&EN Northeast News Bureau, pp. 16-21, 2002.
David J. Kemp et al., Direct immunoassay for detecting *Escherichia coli* colonies that contain polypeptides encoded by cloned DNA segments, PNAS, vol. 78(7):4520-4524, 1981.
Cheng-Ting Chien et al., The two-hybrid system: A method to identify and clone genes for proteins that interact with a protein of interest, PNAS, vol. 88:9578-9582, 1991.
David M. Helfman et al., Identification of clones that encode chicken tropomyosin by direct immunological screening of a cDNA expression library, PNAS, vol. 80:31-35, 1983.
Maria Dani, Biological Libraries, J. of Receptor & Signal Transduction Research, vol. 21(4):447-468, 2001.

(Continued)

*Primary Examiner*—Andrew D Kosar
*Assistant Examiner*—Satyanarayana R Gudibande
(74) *Attorney, Agent, or Firm*—Roger W. Herrell, Jr.

(57) ABSTRACT

Combinatorially generated peptides are provided that have binding affinity for polymethylmethacrylate (PMMA). The peptides may be used to deliver benefit agents to various PMMA surfaces.

4 Claims, 6 Drawing Sheets

OTHER PUBLICATIONS

Genencor International, Bio Conference, San Francisco, California, Jun. 8, 2004—Meeting Presentation, pp. 1-29.

Nils B. Adey et al., Characterization of Phage That Bind Plastic From Phage-Displayed Random Peptide Libraries, Gene, vol. 156:27-31, 1995.

Archit B. Sanghvi et al., Biomaterials Functionalizing Using a Novel Peptide That Selectively Binds to a Conducting Polymer, Nature, vol. 4:496-502, 2005.

K. Gebhardt et al., Adhesive Peptides Selected by Phage Display: Characterization, Applications and Similarities With Fibrinogen, Peptide Research, vol. (6):269-278, 1996.

Takeshi Serizawa et al., A Peptide Motif Recognizing a Polymer Stereoregularity, J. Am. Chem. Soc., vol. 127:13780-13781, 2005.

* cited by examiner

PMMA BINDING PEPTIDES AND METHODS OF USE

CROSS-REFERENCE TO RELATED APPLICATION

This application claims priority under 35 U.S.C. §119 from U.S. Provisional Application Ser. No. 60/750,548, filed Dec. 15, 2005.

FIELD OF THE INVENTION

The invention relates to peptide based reagents having binding affinity for polymethylmethacrylate polymers.

BACKGROUND OF THE INVENTION

Polymethylmethacrylate (PMMA) is a clear polymer developed as a glass substitute. It is commonly referred to as acrylic glass or acrylic and marketed under trademarks such as: Plexiglas™, Perspex™, Acrylite™, Acrylplast™ and Lucite™. PMMA has several advantages over silicon glass. Its density is less than half of its silicon counterpart. PMMA does not shatter. It can be formed at relatively low temperatures. These and other qualities have led engineers to adapt PMMA to other purposes beyond glass replacement. Nevertheless, PMMA is still commonly used for its original purpose, it is found in large windows, aquariums, and vehicle rear lights. However, it is also found in places that glass would never be considered a suitable material. For example it is used as a bone replacement, dentures, and paint coating.

Some physical properties of PMMA are undesirable for a given application. In theses circumstances a coating is applied to mask the undesirable property. For example, PMMA is hydrophobic, when used as an intraocular lens it must be coated to make the surface hydrophilic. Also, PMMA tends to carry a static charge, in some circumstances the charge can build to the point of fracture. DuPont's Zelek-NK™ antistatic coating was developed to counter this tendency.

The ubiquitous use of PMMA in industry makes it a prime material candidate for a variety of applications where the PMMA comprises some or all of a surface. One of the drawbacks to using PMMA as surface is that materials that bind to PMMA are specific and lack flexibility as binding agents. So for example where a new coating for PMMA is desired, a new search for a PMMA binding molecule with the desired property must be conducted. The resulting search is costly in both time and resources and not guaranteed to be successful. A system that is flexible and can be easily tailored for a variety of materials to be bound to PMMA is needed. The use of peptides as linkers or binders to PMMA offers some potential in this regard.

Peptides having a binding affinity to polymer and plastic surfaces are known. For example, Adey et al., (*Gene* 156:27-31 (1995)) describe peptides that bind to polystyrene and polyvinyl chloride surfaces. Additionally, peptides that bind to polyurethane (Murray et al., U.S. Patent Application Publication No. 2002/0098524), polyethylene terephthalate (O'Brien et al., copending and commonly owned U.S. Patent Application Publication No. 2005/0054752), and polystyrene, polyurethane, polycarbonate, and nylon (Grinstaff et al., U.S. Patent Application Publication No. 2003/0185870) have been reported. However, the use of such peptides to target PMMA surfaces has not been described.

There remains a need therefore for a peptide based reagent that binds PMMA that offers flexibility in bring a wide variety of materials to the PMMA surface with minimum investment in redesign. Applicants have solved the stated problem by providing peptide reagents comprising PMMA binding peptides (PmBP). The PMMA binding peptides of the invention may be modified with other functional or binding peptides allowing for the delivery of benefit agents to the PMMA surface or for the use of the reagents to adhere PMMA containing surfaces.

SUMMARY OF THE INVENTION

The present invention provides PMMA binding peptides that may be incorporated into peptide based reagents useful for delivering functional compounds to a PMMA surface. The PMMA binding peptides may comprise active domains that have linker or other functionality or target binding domains that bind various benefit agents that are delivered to the PMMA surface.

Accordingly, in one embodiment the invention provides a peptide reagent having a general structure selected from the group consisting of:

| | |
|---|---|
| $PMMA_m\text{-}(PmBP)_n;$ | a) |
| $PMMA_m\text{-}(PmBP\text{-}BA_p)_n;$ | b) |
| $PMMA_m\text{-}(PmBP\text{-}AD)_n;$ | c) |
| $PMMA_m\text{-}(PmBP\text{-}TBD)_n;$ and | d) |
| $PMMA_m\text{-}(PmBP\text{-}L\text{-}BA)_n;$ and | e) |
| $PMMA_m\text{-}[(PmBP)_q\text{-}(L)_x\text{-}(PmBP)_r]_n\text{-}L\text{-}BA;$ | f) | wherein:
i) PMMA is a PMMA moiety
ii) PmBP is a PMMA binding peptide having a PMMA binding domain;
iii) BA is at least one benefit agent;
iv) AD is at least one active domain incorporated into a PMMA binding peptide;
v) TBD is at least one target binding domain incorporated into a PMMA binding peptide;
vi) L is a linker molecule;
vii) m=the number of PMMA moieties available for binding;
viii) n=is less than or equal to m;
xi) p=1-20;
x) x=1-20; and
xi) r=1-50.

In an alternate embodiment the invention provides a peptide reagent having the general structure:

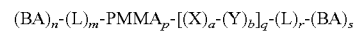

Wherein:
i) BA is a benefit agent;
ii) PMMA is a PMMA moiety;
iii) L is a linker molecule;
iv) X is a PMMA peptide binding domain;
v) Y is an active domain; and
vi) wherein a, b, m, n, p, q, r, and s are non-negative integers wherein, b, n, r, and s may be 0; and
a, p and q will at least be 1.

In another embodiment the invention provides a method for binding a substrate comprising PMMA to a target comprising:
- a) providing a peptide reagent of the invention: and
- b) contacting the peptide reagent of (a) with a substrate comprising a PMMA moiety under conditions whereby the peptide reagent binds to the PMMA moiety.

Similarly the invention provides a method for delivering a benefit agent to a substrate comprising PMMA comprising:
- a) providing the peptide reagent of the invention having a benefit agent: and
- b) contacting the peptide reagent of (a) with a substrate comprising a PMMA moiety under conditions whereby the peptide reagent binds to the PMMA moiety, whereby the benefit agent is delivered to the substrate.

In an alternate embodiment the invention provides a method for adhering two surfaces comprising:
- a) providing a first surface comprising PMMA comprising a first peptide regent having the general formula;

(PmBP-AD1)

wherein:
    - i) PmPB is a PMMA binding peptide; and
    - ii) AD1 is a first active domain;
- b) providing a second surface comprising a target molecule comprising a second peptide reagent have the general formula;

(TBP-AD2)

wherein:
    - iii) TBP is a target binding peptide; and
    - iv) AD2 is a second active domain having affinity for the first active domain;
- c) juxtaposing the first and second surfaces wherein the first and second peptide reagents adhere to each other through the first and second active domains, whereby the surfaces are adhered.

In a similar embodiment the invention provides a method for adhering two surfaces comprising:
- a) providing a first surface comprising a first target molecule comprising a first peptide regent having the general formula;

(TBP1-AD)

wherein:
    - i) TBP1 is a first target binding peptide; and
    - ii) AD is an active domain having binding affinity for PMMA;
- b) providing a second surface comprising a second target molecule comprising a second peptide reagent have the general formula;

(TBP2-AD)

wherein:
    - iii) TBP2 is a second target binding peptide; and
    - iv) AD is an active domain having binding affinity for PMMA;
- c) juxtaposing the first and second surfaces in the presence of a PMMA moiety wherein the first and second peptide reagents adhere to the PMMA moiety through the active domain, whereby the surfaces are adhered.

Additionally the invention provides a PMMA binding peptide having an amino acid sequence selected from the group consisting of SEQ ID NO's: 1-12.

BRIEF DESCRIPTION OF THE FIGURES AND SEQUENCE DESCRIPTIONS

Figure 1A:
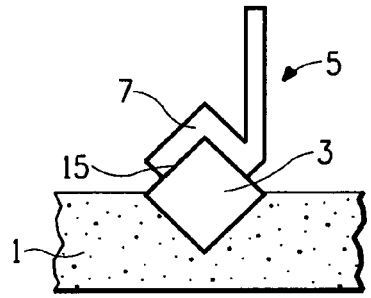
FIG. 1 is a set of panels A-E which depict embodiments of the present invention as they are bound to a surface containing, in whole or in part, PMMA particles.
Figure 1B:
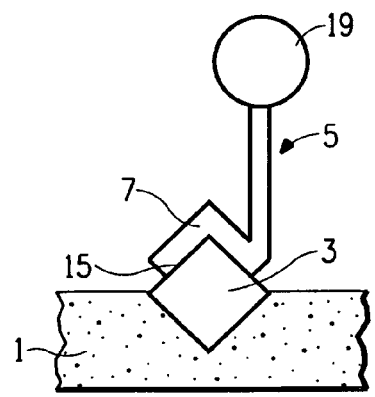
Figure 1C:
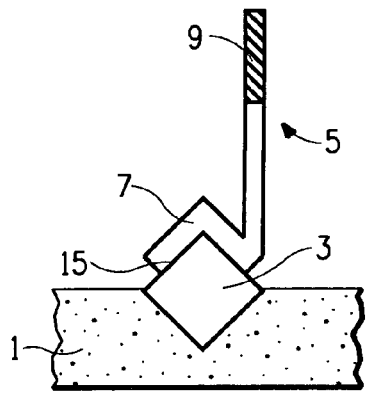
Figure 1D:
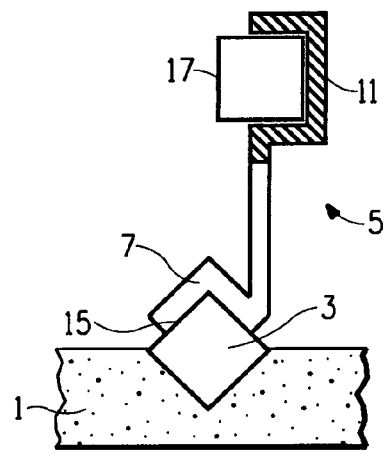
Figure 1D:
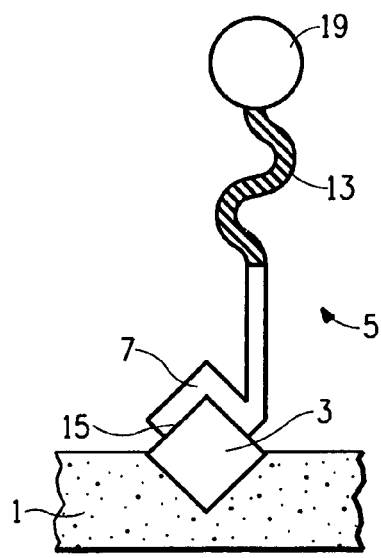

SEQ ID NOs: 1-12 are PMMA binding peptide sequences.

SEQ ID NOs:13-41 are antimicrobial peptides sequences.

SEQ ID NOs: 42-66 are pigment binding peptides sequences.

SEQ ID NOs: 67-79 are print media binding peptide sequences: SEQ ID NOs: 67 and 68 bind to cotton fabric, SEQ ID NOs: 67 and 69 bind to polyester/cotton fabric, SEQ ID NOs: 67, and 70-72 bind to HAMERMILL® paper, SEQ ID NOs: 74-78 bind to cellulose, and SEQ ID NO: 79 binds to poly(ethylene terephthalate).

SEQ ID NOs: 80-175 are body surface binding peptide sequences: SEQ ID NOs: 80-87 are skin-binding peptide sequences, SEQ ID NOs: 88-175 are hair binding peptide sequences and SEQ ID NOs: 88 and 89 bind nails as well as hair.

SEQ ID NO:176 is the amino acid sequence of the Caspase 3 cleavage site that my be used as a peptide linker domain.

SEQ ID NOs: 177-179 are amino acid sequences of peptide linker domains.

A Sequence Listing is provided herewith on Compact Disk. The contents of the Compact Disk containing the Sequence Listing are hereby incorporated by reference in compliance with 37 CFR 1.52(e). The Compact Disks are submitted in triplicate and are identical to one another. The disks are labeled "Copy 1—Sequence Listing", "Copy 2—Sequence Listing", and CRF. The disks contain the following file: CL2828.ST25 having the following size: 40,000 bytes and which was created Nov. 20, 2006.

DETAILED DESCRIPTION OF THE INVENTION

The present invention provides variable coatings for PMMA substrates and surfaces. More specifically, the present invention provides peptide sequences that bind PMMA with a high affinity. These peptides can be bound covalently or otherwise to known substances to adapt PMMA for a variety of uses. Additionally, the present invention provides methods to develop and produce such peptides.

The following definitions and abbreviations are to be used for the interpretation of the claims and the specification.

"BA" means benefit agent.

"PMMA" means polymethylmethacrylate

"PmBP" is a PMMA binding peptide

"PBP" means pigment-binding peptide.

The term "peptide" refers to two or more amino acids joined to each other by peptide bonds or modified peptide bonds.

The term "body surface" will mean any surface of the human body that may serve as a substrate for the binding of a peptide carrying a benefit agent. Typical body surfaces include but are not limited to hair, skin, nails, teeth, gums, and corneal tissue.

The term "benefit agent' is a general term applying to a compound or substance that may be coupled with a complex of PMMA and PMMA binding peptide in order to provide a desirable characteristic of the benefit agent to the complex. In the most general sense a benefit agent may be any element, molecule or compound that is not PMMA or a PMMA-binding peptide. Benefit agents typically include colorants such as pigments and dyes as well as pharmaceuticals, markers, conditioners, and fragrances.

The term "hair" as used herein refers to human hair, eyebrows, and eyelashes.

The term "skin" as used herein refers to human skin, or pig skin, Vitro-Skin® and EpiDerm™ which are substitutes for human skin. Skin as used herein as a body surface will generally comprise a layer of epithelial cells and may additionally comprise a layer of endothelial cells.

The term "nails" as used herein refers to human fingernails and toenails.

The terms "coupling" and "coupled" as used herein refer to any chemical association and includes both covalent and non-covalent interactions.

The term "pigment" refers to an insoluble, organic or inorganic colorant.

The term "print medium" refers to any substrate suitable for printing.

The term "dispersant" as used herein refers to a substance that stabilizes the formation of a colloidal solution of solid pigment particles in a liquid medium.

The term "PMMA binding peptide" refers to a peptide having specific affinity for PMMA. The PMMA binding peptide will typically be short ranging from about 7 to about 50 amino acids in length and may be generated recombinantly, synthetically or may be selected by combinatorial means. PMMA binding peptides may comprise various subdomains including but not limited to active domains, target domains and linker domains. Within any given PMMA binding peptide there resides a "PMMA binding domain" having affinity to PMMA. Any given PMMA binding peptide may contain only the PMMA binding domain or may contain this domain in conjunction with active or target domains having different functionality.

The term "active domain" as used herein applies to a subsequence of amino acids within a PMMA binding peptide. An active domain is a portion of the PMMA binding peptide that is not responsible for PMMA binding but provides additional functionality or benefit. In one embodiment for example an active domain may have antimicrobial functionality. In anther embodiment the active domain may have a linker function between two other domains or between the peptide and a benefit agent. In another embodiment the active domain may serve to bind a specific target analyte (target domain).

The term "linking domain" or "linker domain" as used herein applies to a particular of active domain that is used to either link two domains together, as a separator between two domains, or a domain and a terminal end. Linking domains may have a function beyond joining or separating two features of a peptide.

The term "target binding domain" as used herein applies to a particular type of peptide active domain that binds a target molecule, element, compound, or complex. The binding substrate for the target binding domain is referred to herein as the "target". Typical targets will include but are not limited to biological analytes, (cells, cell membrane fractions, viral proteins, proteins, antibodies, antibody fragments, nucleic acids and the like), plant fibers, synthetic fibers, as well as organic and inorganic target complexes that will typically be found on surfaces or in print media. All target binding domains are active domains. A "body surface binding domain" is a target domain that has specific affinity for a body surface such as hair, skin, nails, teeth and the like. Similarly a "print media binding domain" will function to bind the elements of print media such as paper and other ink receptive surfaces. Within the context of print media domains there may be those domains that bind cellulose or cotton or other plant fibers. Additionally the target domains of the invention may be selected to bind specific benefit agents such as colorants (pigments, dyes) and conditioners or any other organic or inorganic complex.

"PMMA moiety" means a discrete substance comprising polymethylmethacrylate that serves as a binding site for a PMMA binding peptide. PMMA moieties may make up a PMMA film, or be comprised within various PMMA coatings or surfaces and substrates.

The term "linker" or "spacer" or 'linker molecule" or "spacer molecule" will be used interchangeably and will mean a molecule or compound used to bind a benefit agent to the PMMA-peptide complex. Any material that can bind said benefit agent to the complex can be used, including peptide based molecules. A linker molecule is distinct from a linker domain in that linker domains are inherently part of, or are proposed to be part of a peptide further comprising a PMMA-binding domain. A linker molecule, in whole or in part, may be identical to a linking domain, but a linking molecule does not contain a PMMA-binding domain.

As referred to herein a substance has "binding functionality" when it demonstrates specific affinity for a substance or target.

As referred to herein a substance has "catalytic functionality" when it demonstrates the ability to catalyze a chemical reaction As referred to herein a substance has "antimicrobial functionality when it demonstrates the ability to kill microbial cell populations.

As used herein the term "surface" when used in conjunction with a PMMA moiety means the point of contact for the PMMA moiety. Surfaces of the invention will typically be coated with PMMA or may themselves comprise PMMA moieties. Surfaces may take the form of solid support, a bead, a microsphere, a sheet, or a fiber. In some instances the surface of the invention may be layered or juxtaposed on a "secondary surface". A "secondary surface" will typically be coated or layers with the PMMA surfaces of the invention.

The term "diblock structure" as used herein refers to a composition that consists of two different units or blocks, each serving a specific function. The peptide-based diblock polymers of the present invention consist of a PMMA-binding peptide block coupled to a substrate, or a PMMA-binding peptide block coupled to a benefit agent. The diblock polymer may contain multiple copies of the peptide block.

The term "triblock structure" as used herein refers to a pigment dispersant that consists of three different units or blocks, each serving a specific function. The peptide-based triblock structure of the present invention consists of a substrate-block, PMMA-binding peptide block, and a benefit agent block. The triblock structure may contain multiple copies of any of the peptide blocks.

The term "stringency" as it is applied to the selection of PMMA binding peptides, hair-binding, skin-binding, and nail-binding peptides of the present invention, refers to the concentration of the eluting agent (usually detergent) used to elute peptides from the substrate to which they are bound or for which they have affinity. Higher concentrations of the eluting agent provide more stringent conditions.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "expression", as used herein, refers to the transcription and stable accumulation of sense (mRNA) or anti-sense RNA derived from the nucleic acid fragment of the invention. Expression may also refer to translation of mRNA into a polypeptide.

The term "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "host cell" refers to cell which has been transformed or transfected, or is capable of transformation or transfection by an exogenous polynucleotide sequence.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "phage" or "bacteriophage" refers to a virus that infects bacteria. Altered forms may be used for the purpose of the present invention. The preferred bacteriophage is derived from the "wild" phage, called M13. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

Standard recombinant DNA and molecular cloning techniques used herein are well known in the art and are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Cold Press Spring Harbor, N.Y. (1984); and by Ausubel, F. M. et al., Current Protocols in Molecular Biology, published by Greene Publishing Assoc. and Wiley-Interscience (1987).

The present invention relates to peptides and peptide reagents that have specific binding affinity to PMMA in various conformations including complexes of the PMMA binding peptides linked to benefit agents, and optionally where the PMMA binding peptides comprise active peptide domains or target binding domains having binding or other functionality for other substances or surfaces. The PMMA peptide regent of the invention may take a variety of forms including those represented by the following structures:

a) $PMMA_m$-$(PmBP)_n$;

b) $PMMA_m$-$(PmBP$-$BA_p)_n$;

c) $PMMA_m$-$(PmBP$-$AD)_n$;

d) $PMMA_m$-$(PmBP$-$TBD)_n$; and e) $PMMA_m$-$(PmBP$-$L$-$BA)_n$; and f) $PMMA_m$-$[(PmBP)_q$-$(L)_x$-$(PmBP)_r]_n$-$L$-$BA$;

wherein:
i) PMMA is a PMMA moiety
ii) PmBP is a PMMA binding peptide having a PMMA binding domain;
iii) BA is at least one benefit agent;
iv) AD is at least one active domain incorporated into a PMMA binding peptide;
v) TBD is at least one target binding domain incorporated into a PMMA binding peptide;
vi) L is a linker molecule;
vii) m=the number of PMMA moieties available for binding;
viii) n=is less than or equal to m;
xi) p=1-20;
x) x=1-20; and
xi) r=1-50.

Alternatively the PMMA peptides reagents of the invention may be configured according formula:

$(BA)_n$-$(L)_m$-$PMMA_p$-$[(X)_a$-$(Y)_b]_q$-$(L)_r$-$(BA)_s$

Wherein:
i) BA is a benefit agent;
ii) PMMA is a PMMA moiety;
iii) L is a linker molecule;
iv) X is a PMMA peptide binding domain;
v) Y is an active domain; and vi) wherein a, b, m, n, p, q, r, and s are non-negative integers wherein, b, n, r, and s may be 0; and
a, p and q will at least be 1.

PMMA Moieties

A PMMA (poly(methyl methacrylate)) moiety, as defined herein, is the binding site of a PMMA-binding peptide on a surface. The PMMA moiety may be incorporated into a surface in various ways. For example, the surface may be the surface of a PMMA substrate. Alternatively, the PMMA moiety may be imbedded into the surface of another material, such as a polymer, or coated on the surface of another material, such as a metal, polymer, glass, cloth, and the like. The PMMA moiety may comprise a PMMA polymer or a copolymer of methyl methacrylate with one or more monomers such as other acrylates, styrene, acrylonitrile, vinyl acetate, vinyl chloride, vinylidene chloride, and butadiene.

PMMA is prepared by the polymerization of the monomer methyl methacrylate, which is available from many commercial suppliers, such as Aldrich (Milwaukee, Wis.), ICI Acrylics (Beaumont, Tex.), CYRO Industries (Rockaway, N.J.), Total Specialty Chemicals, Inc (New Canaan, Conn.), and Degussa Corp. (Parsippani, N.J.). Methyl methacrylate may be polymerized using methods known in the art, such as radical polymerization, anionic polymerization, or group transfer polymerization (Ullmann's Encyclopedia of Industrial Chemistry, 6$^{th}$ edition, 2003, Wiley-VCH Verlag GmbH and Co., Weinheim, Germany, Vol. 28, pp. 377-389). For example, radical polymerization may be carried out homogeneously (i.e., bulk or solution polymerization) or heterogeneously (i.e., suspension or emulsion polymerization). The radical polymerization may be initiated using radiation, heat, or chemical initiators, such as azo compounds or organic peroxy compounds. Copolymers may be produced by these methods using a mixture of the desired monomers.

The PMMA polymer may be produced in various shapes or forms, such as beads, microspheres, sheets, rods, tubes, films, plates, rings, fiber, and microfilament, using injection molding, extrusion, and casting techniques, which are well known in the art. Additionally, PMMA in various shapes is available commercially from companies such as CRYO Industries and Bang Laboratories (Fishers, Ind.).

In one embodiment, the PMMA polymer or copolymer is coated onto another surface, such as metal, polymer, glass, cloth, and the like, using methods known in the art, such as spraying, brushing, dip coating and casting.

In another embodiment, the PMMA polymer or copolymer is imbedded into the surface of another material, such as another polymer. This may be done by adding particles, beads, or fragments of PMMA material into the other polymer as it cures.

In another embodiment, a PMMA copolymer is used as a dispersant for pigments or other insoluble particles, including metallic and semiconductor nanoparticles. The copolymer may be a random copolymer or a structured copolymer (i.e., a nonrandom block copolymer). Preferred random dispersants include methyl methacrylate copolymers with other acrylates or styrene. Most preferred are structured polymer dispersants, which include AB, BAB and ABC block copolymers, branched polymers and, graft polymers. Preferably these copolymers comprise methyl methacrylate with one or more monomers such as acrylate, methacrylate, butyl methacrylate, 2-ethylhexyl methacrylate, benzyl methacrylate, phenoxyethyl acrylate, and ethoxytriethyleneglycolmethacrylate, such as those described by Nigan (U.S. Patent Application Publication No. 2004/0232377). Some useful structured polymer dispersants are disclosed in U.S. Pat. No. 5,085,698, EP-A-0556649 and U.S. Pat. No. 5,231,131.

Identification of PMMA-Binding Peptides

Peptides having affinity for PMMA, referred to herein as PMMA-binding peptides (PmBP), are peptide sequences that bind strongly to a PMMA moiety. The PMMA-binding peptides of the invention are from about 7 amino acids to about 50 amino acids, more preferably, from about 7 amino acids to about 25 amino acids, most preferably from about 7 to about 20 amino acids in length. Suitable PMMA-binding peptides may be selected using methods that are well known in the art.

The PMMA-binding peptides may be generated randomly and then selected against a PMMA substrate based upon their binding affinity for PMMA, as described by O'Brien et al. (copending and commonly owned U.S. Patent Application Publication No. 2005/0054752), Adey et al., (*Gene* 156:27-31, (1995)), Murray et al. (U.S. Patent Application Publication No. 2002/0098524) and Grinstaff et al. (U.S. Patent Application Publication No. 2003/0185870), all of which are incorporated herein by reference. The generation of random libraries of peptides is well known and may be accomplished by a variety of techniques including, bacterial display (Kemp, D. J.; *Proc. Natl. Acad. Sci. USA* 78(7):4520-4524 (1981), and Helfman et al., *Proc. Natl. Acad. Sci. USA* 80(1):31-35, (1983)), yeast display (Chien et al., *Proc Natl Acad Sci USA* 88(21):9578-82 (1991)), combinatorial solid phase peptide synthesis (U.S. Pat. No. 5,449,754, U.S. Pat. No. 5,480,971, U.S. Pat. No. 5,585,275, U.S. Pat. No. 5,639,603), and phage display technology (U.S. Pat. No. 5,223,409, U.S. Pat. No. 5,403,484, U.S. Pat. No. 5,571,698, U.S. Pat. No. 5,837,500). Techniques to generate such biological peptide libraries are well known in the art. Exemplary methods are described in Dani, M., *J. of Receptor & Signal Transduction Res.*, 21(4): 447-468 (2001), Sidhu et al., *Methods in Enzymology* 328: 333-363 (2000), and *Phage Display of Peptides and Proteins, A Laboratory Manual*, Brian K. Kay, Jill Winter, and John McCafferty, eds.; Academic Press, NY, 1996. Additionally, phage display libraries are available commercially from companies such as New England BioLabs (Beverly, Mass.).

A preferred method to randomly generate peptides is by phage display. Phage display is an in vitro selection technique in which a peptide or protein is genetically fused to a coat protein of a bacteriophage, resulting in display of fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". In its simplest form, biopanning is carried out by incubating the pool of phage-displayed variants with a target of interest that has been immobilized on a plate or bead, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

Specifically, the PMMA-binding peptides may be selected using the following method. A suitable library of phage-peptides is generated using the methods described above or the library is purchased from a commercial supplier. After the library of phage-peptides has been generated, they are then contacted with an appropriate amount of the polymer substrate. The library of phage-peptides is dissolved in a suitable solution for contacting the substrate. The test substrate may be suspended in the solution or may be immobilized on a plate or bead. A preferred solution is a buffered aqueous saline solution containing a surfactant. A suitable solution is Tris-buffered saline (TBS) with 0.5% Tween® 20. The solution may additionally be agitated by any means in order to increase the mass transfer rate of the peptides to the polymer substrate, thereby shortening the time required to attain maximum binding.

Upon contact, a number of the randomly generated phage-peptides will bind to the polymer substrate to form a phage-peptide-polymer complex. Unbound phage-peptide may be removed by washing. After all unbound material is removed, phage-peptides having varying degrees of binding affinities for the polymer substrate may be fractionated by selected washings in buffers having varying stringencies. Increasing the stringency of the buffer used increases the required strength of the bond between the phage-peptide and polymer substrate in the phage-peptide-substrate complex.

A number of substances may be used to vary the stringency of the buffer solution in peptide selection including, but not limited to, acidic pH (1.5-3.0); basic pH (10-12.5); high salt concentrations such as $MgCl_2$ (3-5 M) and LiCl (5-10 M); water; ethylene glycol (25-50%); dioxane (5-20%); thiocyanate (1-5 M); guanidine (2-5 M); urea (2-8 M); and various concentrations of different surfactants such as SDS (sodium dodecyl sulfate), DOC (sodium deoxycholate), Nonidet P-40, Triton X-100, Tween® 20, wherein Tween® 20 is preferred. These substances may be prepared in buffer solutions including, but not limited to, Tris-HCl, Tris-buffered saline, Tris-borate, Tris-acetic acid, triethylamine, phosphate buffer, and glycine-HCl, wherein Tris-buffered saline solution is preferred.

It will be appreciated that phage-peptides having increasing binding affinities for the PMMA substrate may be eluted by repeating the selection process using buffers with increasing stringencies. The eluted phage-peptides can be identified and sequenced by any means known in the art.

In one embodiment, the following method for generating the PMMA-binding peptides of the present invention may be used. A library of combinatorially generated phage-peptides is contacted with PMMA to form phage peptide-substrate complexes. The phage-peptide-substrate complex is separated from uncomplexed peptides and unbound substrate, and the bound phage-peptides from the phage-peptide-substrate complexes are eluted from the complex, preferably by acid treatment. Then, the eluted phage-peptides are identified and sequenced. To identify peptide sequences that bind to PMMA but not to other substrates, a subtractive panning step may be added. Specifically, the library of combinatorially generated phage-peptides is first contacted with the non-target to remove phage-peptides that bind to it. Then, the non-binding phage-peptides are contacted with PMMA and the above process is followed. Alternatively, the library of combinatorially generated phage-peptides may be contacted with the non-target and PMMA simultaneously. Then, the phage-peptide-substrate complexes are separated from the phage-peptide-non-target complexes and the method described above is followed for the desired phage-substrate complexes.

Alternatively, a modified phage display screening method for isolating peptides with a higher affinity for polymer substrates may be used. In the modified method, the phage-peptide-substrate complexes are formed as described above. Then, these complexes are treated with an elution buffer. Any of the elution buffers described above may be used. Preferably, the elution buffer is an acidic solution. Then, the remaining, elution-resistant phage-peptide-substrate complexes are used to directly infect/transfect a bacterial host cell, such as *E. coli* ER2738. The infected host cells are grown in an appropriate growth medium, such as LB (Luria-Bertani) medium, and this culture is spread onto agar, containing a suitable growth medium, such as LB medium with IPTG (isopropyl β-D-thiogalactopyranoside) and S-Gal™. After growth, the plaques are picked for DNA isolation and sequencing to identify the peptide sequences with a high binding affinity for the substrate of interest. Alternatively, PCR may be used to identify the elution-resistant phage-peptides from the modified phage display screening method, described above, by directly carrying out PCR on the phage-peptide-substrate complexes using the appropriate primers, as described by Janssen et al. in U.S. Patent Application Publication No. 2003/0152976, which is incorporated herein by reference.

Production of PMMA-Binding Peptides

The PMMA-binding peptides of the present invention may be prepared using standard peptide synthesis methods, which are well known in the art (see for example Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). Additionally, many companies offer custom peptide synthesis services.

Alternatively, the PMMA-binding peptides of the present invention may be prepared using recombinant DNA and molecular cloning techniques. Genes encoding the PMMA-binding peptides may be produced in heterologous host cells, particularly in the cells of microbial hosts, as described by Huang et al. (U.S. Patent Application Publication No. 2005/0050656) and O'Brien et al., supra.

Preferred heterologous host cells for expression of the binding peptides of the present invention are microbial hosts that can be found broadly within the fungal or bacterial families and which grow over a wide range of temperature, pH values, and solvent tolerances. Because transcription, translation, and the protein biosynthetic apparatus are the same irrespective of the cellular feedstock, functional genes are expressed irrespective of carbon feedstock used to generate cellular biomass. Examples of host strains include, but are not limited to, fungal or yeast species such as *Aspergillus, Trichoderma, Saccharomyces, Pichia, Candida, Hansenula,* or bacterial species such as *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*.

A variety of expression systems can be used to produce the peptides of the present invention. Such vectors include, but are not limited to, chromosomal, episomal and virus-derived vectors, e.g., vectors derived from bacterial plasmids, from bacteriophage, from transposons, from insertion elements, from yeast episoms, from viruses such as baculoviruses, retroviruses and vectors derived from combinations thereof such as those derived from plasmid and bacteriophage genetic elements, such as cosmids and phagemids. The expression system constructs may contain regulatory regions that regulate as well as engender expression. In general, any system or vector suitable to maintain, propagate or express polynucleotide or polypeptide in a host cell may be used for expression in this regard. Microbial expression systems and expression vectors contain regulatory sequences that direct high level expression of foreign proteins relative to the growth of the host cell. Regulatory sequences are well known to those skilled in the art and examples include, but are not limited to, those which cause the expression of a gene to be turned on or off in response to a chemical or physical stimulus, including the presence of regulatory elements in the vector, for example, enhancer sequences. Any of these can be used to construct chimeric genes for production of the any of the binding peptides of the present invention. These chimeric genes can then be introduced into appropriate microorganisms via transformation to provide high level expression of the peptides.

Vectors or cassettes useful for the transformation of suitable host cells are well known in the art. Typically the vector or cassette contains sequences directing transcription and translation of the relevant gene, one or more selectable markers, and sequences allowing autonomous replication or chromosomal integration. Suitable vectors comprise a region 5' of the gene, which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Selectable marker genes provide a phenotypic trait for selection of the transformed host cells such as tetracycline or ampicillin resistance in *E. coli*.

Initiation control regions or promoters which are useful to drive expression of the chimeric gene in the desired host cell are numerous and familiar to those skilled in the art. Virtually any promoter capable of driving the gene is suitable for producing the binding peptides of the present invention including, but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

The vector containing the appropriate DNA sequence as described supra, as well as an appropriate promoter or control sequence, may be employed to transform an appropriate host to permit the host to express the peptide of the present invention. Cell-free translation systems can also be employed to produce such peptides using RNAs derived from the DNA constructs of the present invention. Optionally, it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the production host. Methods for choosing appropriate signal sequences are well known in the art (see for example EP 546049 and WO 9324631). The secretion signal DNA or facilitator may be located between the expression-controlling DNA and the instant gene or gene fragment, and in the same reading frame with the latter.

Active Domains

As noted above active domains are peptide portions of the PMMA binding peptide that convey various additional functionality to the peptide. Any sequence of amino acids may be used as an active domain, including, but not limited to those functioning as a linker, those having binding functionality, having catalytic functionality and those having antimicrobial functionality.

An antimicrobial active domain may be particularly desirable if the PMMA moiety part of the diblock was for instance part of a kitchen countertop surface. Such antimicrobial sequences are well known in the art. Any peptide based antimicrobial sequence could be used as an active domain in the above embodiment. As non-limiting examples table 1 provides possible antimicrobial active domain sequences.

TABLE 1

Antimicrobial active domain sequences.

| Species of origin | SEQ ID NO. | Sequence |
|---|---|---|
| Artificial | 13 | PKGLKKLLKGLKKLLKL |
| Artificial | 14 | KGLKKLLKGLKKLLKL |
| Artificial | 15 | KGLKKLLKLLKKLLKL |
| Artificial | 16 | LKKLLKLLKKLLKL |
| Artificial | 17 | LKKLLKLLKKLL |
| Artificial | 18 | VAKKLAKLAKKLAKLAL |
| Artificial | 19 | FAKLLAKALKKLL |
| Artificial | 20 | KGLKKGLKLLKKLLKL |
| Artificial | 21 | KGLKKLLKLGKKLLKL |
| Artificial | 22 | KGLKKLGKLLKKLLKL |
| Artificial | 23 | KGLKKLLKLLKKGLKL |
| Artificial | 24 | KGLKKLLKLLKKLGKL |
| Artificial | 25 | FALALKALKKLKKALKKAL |
| Artificial | 26 | FAKKLAKLAKKLAKLAL |
| Artificial | 27 | FAKLLAKLAKKLL |
| Artificial | 28 | FAKKLAKLALKLAKL |
| Artificial | 29 | FAKKLAKKLL |
| Artificial | 30 | FAKLLAKLAKKVL |
| Artificial | 31 | KYKKALKKLAKLL |
| Artificial | 32 | FALLKALLKKAL |
| Artificial | 33 | KRLFKKLKFSLRKY |
| Artificial | 34 | KRLFKKLLFSLRKY |
| Artificial | 35 | LLLFLLKKRKKRKY |
| H. cecropia | 36 | KWKLFKKIEKVGQNIRDGIIKAGPAVAWGQATQIAK |
| Xenopus | 37 | GIGKFLHSAKKFGKAFVGEIMNS |
| Xenopus | 38 | GIGKFLKKAKKFGKAFVKILKK |
| Bos Taurus | 39 | RLCRIVVIRVCR |
| Bos Sp. | 40 | ILPWKWPWWPWRR |
| H. sapiens | 41 | DSHAKRHHGYKRKFHEKHHSHRGY |

Two sub-types of active domains, target binding domains and linking domains, have been given specific names in the discussion of this present invention. A target binding domain is an active domain that specifically binds to a known target. Target binding sequences are known in the art and can be developed using known techniques as well as techniques described herein. Non-limiting examples of targets to which target binding domains will bind include, pigments, dyes, chemical functional groups, print media, body surfaces (hair, skin, nails, teeth etc.) and biological analytes (cells, receptors, proteins, nucleic acids, viral particles, prions etc.) (see FIGS. 4, 5 and 6 panel D).

A linking domain is an active domain that is specifically used to separate two domains or a domain from a terminal end. Any sequence of amino acids that does not contain a PMMA-binding site can be used as a linking domain. A linking domain can have activity beyond just separating two features of a peptide. A linking domain may provide a specific structure to the separating portion of the peptide. Conversely, a linking domain may also be selected to provide flexibility to the separating portion of the peptide. Additionally the linking domain may be created to specifically change the rheology of the medium the peptide is immersed in. Also the linking domain may be constructed so that it can be cleaved by, or act as the binding site for, a cleaving molecule or enzyme, for the purpose of releasing a portion of the peptide and/or the PMMA from the complex.

Preferred peptide linker domains are composed of the amino acids proline, lysine, glycine, alanine, and serine, and mixtures thereof. In addition, the peptide linker may contain a specific enzyme cleavage site, such as the protease Caspase 3 site, given by SEQ ID NO:176, which allows for the enzymatic removal of a portion of the peptide and/or the PMMA from the complex. The peptide linker may be from 1 to about 50 amino acids, preferably from 1 to about 20 amino acids in length. Examples of peptide linkers include, but are not limited to, SEQ ID NOs:176 to 179. These peptide linkers may be linked to the binding peptide sequence by any method know in the art. For example, the entire binding peptide-peptide linker-diblock may be prepared using the standard peptide synthesis methods described supra. In addition, the binding peptide and peptide linker blocks may be combined using carbodiimide coupling agents (see for example, Hermanson, *Bioconjugate Techniques*, Academic Press, New York (1996)), diacid chlorides, diisocyanates and other difunctional coupling reagents that are reactive to terminal amine and/or carboxylic acid groups on the peptides. Alternatively, the entire binding peptide-peptide linker-diblock may be prepared using the recombinant DNA and molecular cloning techniques described supra. The linker may also be a combination of a peptide linker and an organic linker molecule, which may be prepared using the methods described above. Examples of specific linker peptides are given in table 2 below.

TABLE 2

Linker peptides

| Species of origin | SEQ ID NO. | Sequence |
|---|---|---|
| Artificial | 176 | LESGDEVD |
| Artificial | 177 | TSTSKASTTT TSSKTTTTSS KTTTTTSKTS TTSSSSST |
| Artificial | 178 | GQGGYGGLGS QGAGRGGLGG QG |
| Artificial | 179 | GPGGYGPGQQ |

Target domains of the invention are another type of active domain comprised within the PMMA binding peptide. Target domains will have binding affinity for various substance such as benefit agents (pigments, dyes, print media, biological analtyes, body surfaces (hair, skin, nails, teeth etc.) and the like).

Pigment binding domains are target domains that bind various pigments and colorants. Such pigments have application in the personal care as well as the printing industries. Similarly print media binding domains are target binding domains having specific affinity for various types of print media. Typically the print media will comprise cotton or cellulose targets or may be coated with a polymer such as nylon or PMMA giving rise to cotton, cellulose or polymer binding domains as part of the PMMA binding peptide.

Target domains may be uni-functional having binding affinity for a single target species or multifunctional, having affinity for a variety of targets. For example it may be desirable to combine a pigment binding domain or a print medium binding domain or both into the peptide part of the PMMA-peptide complex of the present invention. Such an embodiment that includes a print-medium binding domain may be particularly desirable if the complex already contains a benefit agent that is a colorant or dye. Pigment-binding peptides and print medium-binding peptides have been identified (See tables 3, 4, and 5, and O'Brien et al., supra, hereby incorporated by reference. The pigment-binding peptides typically comprise at least about 40 mole % of the amino acids: glycine, alanine, valine, leucine, isoleucine, methionine, proline, phenylalanine, and tryptophan Specifically, binding peptides were isolated that have a high affinity for the pigments carbon black, given as SEQ ID NOs:42-45, CROMOPHTHAL® Yellow, given as SEQ ID NOs: 46-53, SUNFAST® Magenta, given as SEQ ID NOs: 55-57, and SUNFAST® Blue, given as SEQ ID NOs: 54, 58-66. The cellulose-binding peptides of the invention comprise at least about 14 mole % of the amino acids: serine, threonine and tyrosine. Binding peptides having a high binding affinity for cellulose (a major component of cotton) include SEQ ID NOs: 73-78. The polyester-binding peptides of the invention comprise at least about 20 mole % of the amino acids: phenylalanine, tryptophan, and tyrosine. Binding peptides having a high affinity for polyester (poly (ethylene terephthalate)) include SEQ ID NO: 79. Additionally, binding peptides were isolated that have a binding affinity for the following print media: cotton, given as SEQ ID NOs: 67 and 68, polyester/cotton, given as SEQ ID NOs: 67 and 69, and printing paper, given as SEQ ID NOs: 67, and 70-72.

TABLE 3

Pigment-Binding Peptides

| Pigment | Designated Peptide Name | Sequence | SEQ ID NO: |
|---|---|---|---|
| Carbon Black | CB-71 | MPPPLMQ | 42 |
| | CB-72 | FHENWPS | 43 |
| | CB-121 | RTAPTTPLLLSL | 44 |
| | CR-122 | WHLSWSPVPLPT | 45 |
| Cromophtal ® Yellow | CY-71 | PHARLVG | 46 |
| | CY-72 | NIPYHHP | 47 |
| | CY-73 | TTMPAIP | 48 |
| | CY-74 | HNLPPRS | 49 |
| | CY-121 | AHKTQMGVRQPA | 50 |
| | CY-122* | ADNVQMGVSHTP | 51 |
| | CY-123* | AHNAQMGVSHPP | 52 |
| | CY-124* | ADYVGMGVSHRP | 53 |
| | CY-125 | SVSVGMKPSPRP | 54 |

TABLE 3-continued

Pigment-Binding Peptides

| Pigment | Designated Peptide Name | Sequence | SEQ ID NO: |
|---|---|---|---|
| Sunfast ® Magenta | SM-71 | YPNTALV | 55 |
| | SM-72 | VATRIVS | 56 |
| | SM-121 | HSLKNSMLTVMA | 57 |
| Sunfast ® Blue | SB-71 | NYPTQAP | 58 |
| | SB-72 | KCCYSVG | 59 |
| | SB-121 | RHDLNTWLPPVK | 60 |
| | SB-122 | EISLPAKLPSAS | 61 |
| | SB-123 | SVSVGMKPSPRP | 54 |
| | SB-124** | SDYVGMRPSPRH | 62 |
| | SB-125** | SDYVGMRLSPSQ | 63 |
| | SB-126** | SVSVGIQPSPRP | 64 |
| | SB-127** | YVSVGIKPSPRP | 65 |
| | SB-128** | YVCEGIHPCPRP | 66 |

*These sequences are analogs of CY-121.
**These sequences are either analogs of SB-123 or are similar to the analogs of SB-123.

TABLE 4

Print Medium-Binding Peptides

| Print Medium | Designated Name | Peptide Sequence | SEQ ID NO: |
|---|---|---|---|
| Cotton fabric | COT-71* | SILPYPY | 67 |
| | COT-72 | STASYTR | 68 |
| Polyester/cotton fabric | P/C-71 | LPVRPWT | 69 |
| | P/C-72* | SILPYPY | 67 |
| Hammermill ® paper | HCP-71 | GNTPSRA | 70 |
| | HCP-72 | HAIYPRH | 71 |
| | HCP-73 | YQDSAKT | 72 |
| | HCP-74* | SILPYPY | 67 |

*These sequences are identical.

TABLE 5

Cellulose and Poly(ethylene terephthalate)-Binding Peptides

| Print Medium Ingredient | Designated Name | Peptide Sequence | SEQ ID NO: |
|---|---|---|---|
| Cellulose | CEL-71 | VPRVTSI | 73 |
| | CEL-72 | MANHNLS | 74 |
| | CEL-73 | FHENWPS | 75 |
| | CEL-121 | THKTSTQRLLAA | 76 |
| | CEL-122 | KCCYVNVGSVFS | 77 |
| | CEL-123 | AHMQFRTSLTPH | 78 |
| Poly(ethylene terephthalate) | PET-121 | GTSDHMIMPFFN | 79 |

Target domains that have binding affinity for body surfaces are particularly useful for the production of personal care compositions comprising colorants, and conditioners with specific binding affinity for the body surface. For example, it may be desirable to attach PMMA-peptide complex of the present invention in either a tri-block form or a di-block form to a body surface such as hair or skin. One method to achieve such a result is to incorporate a target binding domain into the peptide part of the present invention that binds hair, skin or another body surface. Both hair and skin binding domains can be produced by the methods described here, in the co-pending, commonly owned U.S. Ser. No. 10/935,642 (U.S. Patent Application Publication No. 2005/0050656) hereby incorporated by reference and in co-pending, commonly owned U.S. Ser. No. 11/074,473 (U.S. Patent Application Publication No. 2005/0226839) also hereby incorporated by reference. Examples of hair and skin binding domains are shown in Table 6.

TABLE 6

Body Surface Binding Peptide Domains

| Body Surface | SEQ ID NO | Sequence |
|---|---|---|
| Skin | 80 | FTQSLPR |
| Skin | 81 | TPFHSPENAPGS |
| Skin | 82 | KQATFPPNPTAY |
| Skin | 83 | HGHMVSTSQLSI |
| Skin | 84 | LSPSRMK |
| Skin | 85 | LPIPRMK |
| Skin | 86 | HQRPYLT |
| Skin | 87 | FPPLLRL |
| Nail | 88 | ALPRIANTWSPS |
| Nail | 89 | YPSFSPTYRPAF |
| Hair | 90 | YPSFSPTYRPAF |
| Hair | 91 | ALPRIANTWSPS |
| Hair | 92 | LESTPKMK |
| Hair | 93 | SVSVGMKPSPRP |
| Hair | 94 | LDVESYKGTSMP |
| Hair | 95 | RVPNKTVTVDGA |
| Hair | 96 | DRHKSKYSSTKS |
| Hair | 97 | KNFPQQKEFPLS |
| Hair | 98 | QRNSPPAMSRRD |
| Hair | 99 | TRKPNMPHGQYL |
| Hair | 100 | KPPHLAKLPFTT |
| Hair | 101 | NKRPPTSHRIHA |
| Hair | 102 | NLPRYQPPCKPL |
| Hair | 103 | RPPWKKPIPPSE |
| Hair | 104 | RQRPKDHFFSRP |
| Hair | 105 | SVPNK(T or P)VTVDGX |
| Hair | 106 | TTKWRHRAPVSP |
| Hair | 107 | WLGKNRIKPRAS |
| Hair | 108 | SNFKTPLPLTQS |
| Hair | 109 | KELQTRNVVQRE |
| Hair | 110 | GMPAMHWIHPFA |
| Hair | 111 | TPTANQFTQSVP |
| Hair | 112 | AAGLSQKHERNR |
| Hair | 113 | ETVHQTPLSDRP |
| Hair | 114 | LPALHIQRHPRM |
| Hair | 115 | QPSHSQSHNLRS |
| Hair | 116 | RGSQKSKPPRPP |
| Hair | 117 | THTQKTPLLYYH |
| Hair | 118 | TKGSSQAILKST |
| Hair | 119 | DLHTVYH |
| Hair | 120 | HIKPPTR |
| Hair | 121 | HPVWPAI |
| Hair | 122 | MPLYYLQ |
| Hair | 123 | HLTVPWRGGGSAVPFYSHSQITLPNH |
| Hair | 124 | GPHDTSSGGVRPNLHHTSKKEKRENRKVPFYSHSVTSRGNV |
| Hair | 125 | KHPTYRQ |
| Hair | 126 | HPMSAPR |
| Hair | 127 | MPKYYLQ |
| Hair | 128 | MHAHSIA |
| Hair | 129 | TAATTSP |
| Hair | 130 | LGIPQNL |
| Hair | 131 | AKPISQHLQRGS |
| Hair | 132 | APPTPAAASATT |
| Hair | 133 | DPTEGARRTIMT |
| Hair | 134 | EQISGSLVAAPW |
| Hair | 135 | LDTSFPPVPFHA |
| Hair | 136 | LPRIANTWSPS |
| Hair | 137 | RTNAADHPAAVT |
| Hair | 138 | SLNWVTIPGPKI |
| Hair | 139 | TDMQAPTKSYSN |
| Hair | 140 | TIMTKSPSLSCG |
| Hair | 141 | TPALDGLRQPLR |
| Hair | 142 | TYPASRLPLLAP |
| Hair | 143 | AKTHKHPAPSYS |
| Hair | 144 | TDPTPFSISPER |
| Hair | 145 | CAAGCCTCAGCGACCGAATA |
| Hair | 146 | WHDKPQNSSKST |
| Hair | 147 | NEVPARNAPWLV |

TABLE 6-continued

Body Surface Binding Peptide Domains

| Body Surface | SEQ ID NO | Sequence |
|---|---|---|
| Hair | 148 | NSPGYQADSVAIG |
| Hair | 149 | TQDSAQKSPSPL |
| Hair | 150 | TPPELLHGDPRS |
| Hair | 151 | TPPTNVLMLATK |
| Hair | 152 | NTSQLST |
| Hair | 153 | NTPKENW |
| Hair | 154 | NTPASNR |
| Hair | 155 | PRGMLST |
| Hair | 156 | PPTYLST |
| Hair | 157 | TIPTHRQHDYRS |
| Hair | 158 | TPPTHRL |
| Hair | 159 | LPTMSTP |
| Hair | 160 | LGTNSTP |
| Hair | 161 | TPLTGSTNLLSS |
| Hair | 162 | TPLTKET |
| Hair | 163 | QQSHNPP |
| Hair | 164 | TQPHNPP |
| Hair | 165 | STNLLRTSTVHP |
| Hair | 166 | HTQPSYSSTNLF |
| Hair | 167 | SLLSSHA |
| Hair | 168 | QQSSISLSSHAV |
| Hair | 169 | NASPSSL |
| Hair | 170 | HSPSSLR |
| Hair | 171 | K(H, R or N)SHHTH |
| Hair | 172 | E(H, R, or N)SHHTH |
| Hair | 173 | LESTSLL |
| Hair | 174 | TPLTKET |
| Hair | 175 | KQSHNPP |

If the present invention is desired to be used in connection with a hair care composition an effective amount of the complex for use in a hair care composition is herein defined as a proportion of from about 0.01% to about 10%, preferably about 0.01% to about 5% by weight relative to the total weight of the composition. Components of a cosmetically acceptable medium for hair care compositions are described by Philippe et al. in U.S. Pat. No. 6,280,747, and by Omura et al. in U.S. Pat. No. 6,139,851 and Cannell et al. in U.S. Pat. No. 6,013,250, all of which are incorporated herein by reference. For example, these hair care compositions can be aqueous, alcoholic or aqueous-alcoholic solutions, the alcohol preferably being ethanol or isopropanol, in a proportion of from about 1 to about 75% by weight relative to the total weight, for the aqueous-alcoholic solutions. Additionally, the hare care compositions may contain one or more conventional cosmetic or dermatological additives or adjuvants including but not limited to, antioxidants, preserving agents, fillers, surfactants, UVA and/or UVB sunscreens, fragrances, thickeners, wetting agents and anionic, nonionic or amphoteric polymers, and dyes or pigments.

In a number of embodiments the present invention could be used in a skin care composition. Skin care compositions are herein defined as compositions comprising an effective amount of a skin conditioner or a mixture of different skin conditioners in a cosmetically acceptable medium. The uses of these compositions include, but are not limited to, skin care, skin cleansing, make-up, and anti-wrinkle products. If the present invention is desired to be used in connection with a skin care composition an effective amount of the complex for skin care compositions is herein defined as a proportion of from about 0.001% to about 10%, preferably about 0.01% to about 5% by weight relative to the total weight of the composition. This proportion may vary as a function of the type of skin care composition. Suitable compositions for a cosmetically acceptable medium are described by Philippe et al. supra. For example, the cosmetically acceptable medium may be an anhydrous composition containing a fatty substance in a proportion generally of from about 10 to about 90% by weight relative to the total weight of the composition, where the fatty phase containing at least one liquid, solid or semi-solid fatty substance. The fatty substance includes, but is not limited to, oils, waxes, gums, and so-called pasty fatty substances. Alternatively, the compositions may be in the form of a stable dispersion such as a water-in-oil or oil-in-water emulsion. Additionally, the compositions may contain one or more conventional cosmetic or dermatological additives or adjuvants, including but not limited to, antioxidants, preserving agents, fillers, surfactants, UVA and/or UVB sunscreens, fragrances, thickeners, wetting agents and anionic, nonionic or amphoteric polymers, and dyes or pigments.

Benefit Agents

Benefit agents are any material or substance that may be complexed with the PMMA binding peptide in an manner so as to deliver a benefit at the point where the PMMA binding peptide is attached. In the most general sense the benefit agent will be the third component of the tri-block of PMMA and PMMA binding peptide. Any complex, compound or element may be used with the present invention as a benefit agent. If a user of the invention desires to have the features of a benefit agent combined with PMMA then a triblock may be constructed to include the benefit agent in the formation with PMMA and a PMMA-binding peptide. A benefit agent may be selected for the purpose of adding the physical, chemical and/or biological properties of said agent to the PMMA-peptide complex of the present invention. The result of this construct will be said benefit agent closely associated with PMMA and the activity of said benefit agent will be included within the triblock.

The triblock embodiment of this present invention is composed of at least one member of each block element but may also have multiple copies of identical or different members of one, two or all three block elements. Benefit agents can be used singularly or in a plurality. In some embodiments a plurality of peptide blocks or a plurality of PMMA blocks or a plurality of both blocks may be added to a single benefit agent block or a number of benefit agent blocks. For some small benefit agents, for non-limited example, those composed of an element, as many as 10,000 benefit agents could be added to a single PMMA-complex. For some large benefit agents, for non-limiting example, a dye embedded in a plastic bead as many as 10,000 PMMA complexes might be attached to a single benefit agent.

Benefit agents may be inorganic or organic in nature, this includes being polymer or peptide based. They may not be by definition either composed of PMMA or part of a PMMA-binding peptide, since such compositions are defined as categorically other parts of the triblock formation. Some preferred embodiments include benefit agents that are pigments, pharmaceuticals, markers, conditioners, colorants, and fragrances.

Pharmaceuticals.

A pharmaceutical generally means a substance dosed to an organism or thing to treat or prevent a disease or condition. A pharmaceutical benefit agent includes, in a non-limiting sense, the topical, internal or intracellular administration of a compound to an organism as a treatment or a prophylactic. A non-limiting example of this embodiment of the present invention would be the attachment of an anti-acne medication to formulation of the present invention designed to be a skin conditioner. A pharmaceutical benefit agent also includes a treatment to surface or item to prevent an infectious germ from being transmitted after contacting said surface or item. The addition of an antimicrobial compound to a construction of the present invention to be used on countertops would be a non-limiting example of this embodiment. Suitable pharmaceuticals are well known in the art. An extensive list is given by Kabonov et al. in U.S. Pat. No. 6,696,089, which is incorporated herein by reference (in particular, columns 16 to 18). Examples include, but are not limited to, antibacterial agents, antiviral agents, antifungal agents, anti-cancer agents, vaccines, radiolabels, anti-inflammatories, anti-glaucomic agents, local anesthetics, anti-neoplastic agents, antibodies, hormones, and the like.

Markers.

Markers as used and defined herein refer to a class of benefit agents that provide aid in detecting the presence of the PMMA-peptide complex to which they are, or were, attached. The marker benefit agent might be a dye, fluorescent label, radioactive element or some other signal. Radioactive $P^{32}$ is a non-limiting example of this type of marker benefit agent. Also the marker benefit agent might also be a substance that reacts with a dye, fluorescent label or other signal. Biotin used in connection with a labled-streptavidin compound is a non-limited example of this type of marker benefit agent. Additionally a marker benefit agent might also provide, or help to provide aid to detect, the presence or lack of presence of another specific chemical, compound, element or complex. By way of non-limiting example, the marker benefit agent might be a compound that is metabolized by a specific enzyme to produce a metabolite that reacts with a fluorescently labeled phosphine. The Staudinger ligation is a non-limiting example of this type of marker benefit agent.

Conditioners.

Conditioner benefits agents as referred to in discussion of the present invention generally mean benefit agents that provide an improvement to the appearance, texture or quality of the substance they are designed to condition. Conditioner benefit agents may be used with the present invention to condition any substance including but not limited to hair, skin, lips, leather, and upholstery. In the preferred embodiment the present invention is used in combination with a benefit agent that provides a conditioning effect to hair and skin. In the most preferred embodiment said hair and skin are human hair and human skin.

Hair conditioning agents as herein defined are agents which improve the appearance, texture, and sheen of hair as well as increasing hair body or suppleness. In the peptide-based hair conditioners of the present invention, any known hair conditioning agent may be used. Hair conditioning agents are well known in the art, see for example Green et al. (WO 0107009), incorporated herein by reference, and are available commercially from various sources. Suitable examples of hair conditioning agents include, but are not limited to, cationic polymers, such as cationized guar gum, diallyly quaternary ammonium salt/acrylamide copolymers, quaternized polyvinylpyrrolidone and derivatives thereof, and various polyquaternium-compounds; cationic surfactants, such as stearalkonium chloride, centrimonium chloride, and Sapamin hydrochloride; fatty alcohols, such as behenyl alcohol; fatty amines, such as stearyl amine; waxes; esters; nonionic polymers, such as polyvinylpyrrolidone, polyvinyl alcohol, and polyethylene glycol; silicones; siloxanes, such as decamethylcyclopentasiloxane; polymer emulsions, such as amodimethicone; and volumizing agents, such as nanoparticles (e.g., silica nanoparticles and polymer nanoparticles). The preferred hair conditioning agents of the present invention contain amine or hydroxyl functional groups to facilitate coupling to the hair-binding peptides. Examples of preferred conditioning agents are octylamine (CAS No. 111-86-4), stearyl amine (CAS No. 124-30-1), behenyl alcohol (CAS No. 661-19-8, Cognis Corp., Cincinnati, Ohio), vinyl group terminated siloxanes, vinyl group terminated silicone (CAS No. 68083-19-2), vinyl group terminated methyl vinyl siloxanes, vinyl group terminated methyl vinyl silicone (CAS No. 68951-99-5), hydroxyl terminated siloxanes, hydroxyl terminated silicone (CAS No. 80801-30-5), amino-modified silicone derivatives, [(aminoethyl)amino]propyl hydroxyl dimethyl siloxanes, [(aminoethyl)amino]propyl hydroxyl dimethyl silicones, and alpha-tridecyl-omega-hydroxy-poly(oxy-1,2-ethanediyl) (CAS No. 24938-91-8).

Skin conditioning agents as herein defined include, but are not limited to astringents, which tighten skin; exfoliants, which remove dead skin cells; emollients, which help maintain a smooth, soft, pliable appearance; humectants, which increase the water content of the top layer of skin; occlusives, which retard evaporation of water from the skin's surface; and miscellaneous compounds that enhance the appearance of dry or damaged skin or reduce flaking and restore suppleness. In the peptide-based skin conditioners of the present invention, any known skin conditioning agent may be used. Skin conditioning agents are well known in the art, see for example Green et al. supra, and are available commercially from various sources. Suitable examples of skin conditioning agents include, but are not limited to, alpha-hydroxy acids, beta-hydroxy acids, polyols, hyaluronic acid, D,L-panthenol, polysalicylates, vitamin A palmitate, vitamin E acetate, glycerin, sorbitol, silicones, silicone derivatives, lanolin, natural oils and triglyceride esters. The preferred skin conditioning agents of the present invention are polysalicylates, propylene glycol (CAS No. 57-55-6, Dow Chemical, Midland, Mich.), glycerin (CAS No. 56-81-5, Proctor & Gamble Co., Cincinnati, Ohio), glycolic acid (CAS No. 79-14-1, DuPont Co., Wilmington, Del.), lactic acid (CAS No. 50-21-5, Alfa Aesar, Ward Hill, Mass.), malic acid (CAS No. 617-48-1, Alfa Aesar), citric acid (CAS No. 77-92-9, Alfa Aesar), tartaric acid (CAS NO. 133-37-9, Alfa Aesar), glucaric acid (CAS No. 87-73-0), galactaric acid (CAS No. 526-99-8), 3-hydroxyvaleric acid (CAS No. 10237-77-1), salicylic acid (CAS No. 69-72-7, Alfa Aesar), and 1,3 propanediol (CAS No. 504-63-2, DuPont Co., Wilmington, Del.). Polysalicylates may be prepared by the method described by White et al. in U.S. Pat. No. 4,855,483, incorporated herein by reference.

Glucaric acid may be synthesized using the method described by Merbouh et al. (*Carbohydr. Res.* 336:75-78 (2001). The 3-hydroxyvaleric acid may be prepared as described by Bramucci in WO 02012530.

Colorants.

The term colorant generally refers to a coloring agent. Colorants may be chemically organic or inorganic and may include pigments or dyes. The peptide-based colorants of the present invention may be prepared by covalently attaching a specific PMMA-binding peptide to a coloring agent, either directly or via a linker, using any of the coupling methods known in the art (see for example, U.S. Patent Application Publication No. 2005/0226839).

Pigments are a particularly suitable benefit agent. Pigments generally means an insoluble colorant. A wide variety of organic and inorganic pigments alone or in combination may be used in the present invention. Examples of organic pigments include, but are not limited to Cyan, Yellow, Red, Blue, Orange, Magenta, Black, Green, Violet, Light Cyan, and Light Magenta. Preferred organic pigments are carbon black, such as Carbon Black FW18, and colored pigments such as CROMOPHTHAL® Yellow 131AK (Ciba Specialty Chemicals), SUNFAST® Magenta 122 (Sun Chemical) and SUNFAST® Blue 15:3 (Sun Chemical). Examples of inorganic pigments include, but are not limited to finely divided metals, such as copper, iron, aluminum, and alloys thereof; and metal oxides, such as silica, alumina, and titania. Additional examples of suitable pigments are given by Ma et al. in U.S. Pat. No. 5,085,698, incorporated herein by reference.

The preferred coloring agents for use in the skin based applications of the present invention include but are not limited to the following dyes: eosin derivatives such as D&C Red No. 21 and halogenated fluorescein derivatives such as D&C Red No. 27, D&C Red Orange No. 5 in combination with D&C Red No. 21 and D&C Orange No. 10, and the pigments: titanium dioxide, zinc oxide, D&C Red No. 36 and D&C Orange No. 17, the calcium lakes of D&C Red Nos. 7, 11, 31 and 34, the barium lake of D&C Red No. 12, the strontium lake D&C Red No. 13, the aluminum lakes of FD&C Yellow No. 5, of FD&C Yellow No. 6, of D&C Red No. 27, of D&C Red No. 21, of FD&C Blue No. 1, iron oxides, manganese violet, chromium oxide, ultramarine blue, and carbon black.

The preferred coloring agents for use with the present invention in the nail based applications include but are not limited to D&C Red Nos. 8, 10, 30 and 36, the barium lakes of D&C Red Nos. 6, 9 and 12, the calcium lakes of D&C Red Nos. 7, 11, 31 and 34, the strontium lake of D&C Red No. 30 and D&C Orange No. 17 and D&C Blue No. 6. Suitable hair coloring agents for use with the present invention include, but are not limited to dyes, such as 4-hydroxypropylamino-3-nitrophenol, 4-amino-3-nitrophenol, 2-amino-6-chloro-4-nitrophenol, 2-nitro-paraphenylenediamine, N,N-hydroxyethyl-2-nitro-phenylenediamine, 4-nitro-indole, Henna, HC Blue 1, HC Blue 2, HC Yellow 4, HC Red 3, HC Red 5, Disperse Violet 4, Disperse Black 9, HC Blue 7, HC Blue 12, HC Yellow 2, HC Yellow 6, HC Yellow 8, HC Yellow 12, HC Brown 2, D&C Yellow 1, D&C Yellow 3, D&C Blue 1, Disperse Blue 3, Disperse violet 1, eosin derivatives such as D&C Red No. 21 and halogenated fluorescein derivatives such as D&C Red No. 27, D&C Red Orange No. 5 in combination with D&C Red No. 21 and D&C Orange No. 10; and pigments, such as D&C Red No. 36 and D&C Orange No. 17, the calcium lakes of D&C Red Nos. 7, 11, 31 and 34, the barium lake of D&C Red No. 12, the strontium lake of D&C Red No. 13, the aluminum lakes of FD&C Yellow No. 5, of FD&C Yellow No. 6, of D&C Red No. 27, of D&C Red No. 21, and of FD&C Blue No. 1, iron oxides, manganese violet, chromium oxide, titanium dioxide, iron oxides, zinc oxide, barium oxide, ultramarine blue, bismuth citrate, and carbon black particles.

The preferred hair coloring agents of the present invention are D&C Yellow 1 and 3, HC Yellow 6 and 8, D&C Blue 1, HC Blue 1, HC Brown 2, HC Red 5,2-nitro-paraphenylenediamine, N,N-hydroxyethyl-2-nitro-phenylenediamine, 4-nitro-indole, iron oxides, and carbon black.

Fragrances.

A fragrance is a complex, compound or element that releases, a substance which may be perceived by the sense of olfaction or chemical detection in any organism, but preferably, in humans. The object sensed or detected may be a part of or the whole of the fragrance benefit agent. In the preferred embodiment the odor is perceived as desirable to humans. However, some uses may combine the present invention with a fragrance benefit agent that is repellent to a class of organisms, including a class that contains or is humans. Any known fragrance or odor may be use as a benefit agent. It may be desirable to attach a fragrance benefit agent to the PMMA-peptide complex by a bond structure or linking molecule that allows the benefit agent to be released, in part or in whole, so that it may be perceived by a sensing organ or chemical detector.

Numerous fragrances, both natural and synthetic, are well known in the art. For example, Secondini (*Handbook of Perfumes and Flavors*, Chemical Publishing Co., Inc., New York, 1990), incorporated herein by reference, describes many of the natural and synthetic fragrances used in cosmetics. Suitable natural fragrances include, but are not limited, to jasmines, narcissus, rose, violet, lavender, mint, spice, vanilla, anise, amber, orange, pine, lemon, wintergreen, rosemary, basil, and spruce. Suitable synthetic fragrances include, but are no limited to, acetaldehyde, C7 to C16 alcohols, benzyl acetate, butyric acid, citric acid, isobutyl phenyl acetate, linalyl butyrate, malic acid, menthol, phenyl ethyl cinnamate, phenyl propyl formate, tannic acid, terpineol, vanillin, amyl salicylate, benzaldehyde, diphenyl ketone, indole, and the like.

Linker Molecules

Figure 3:
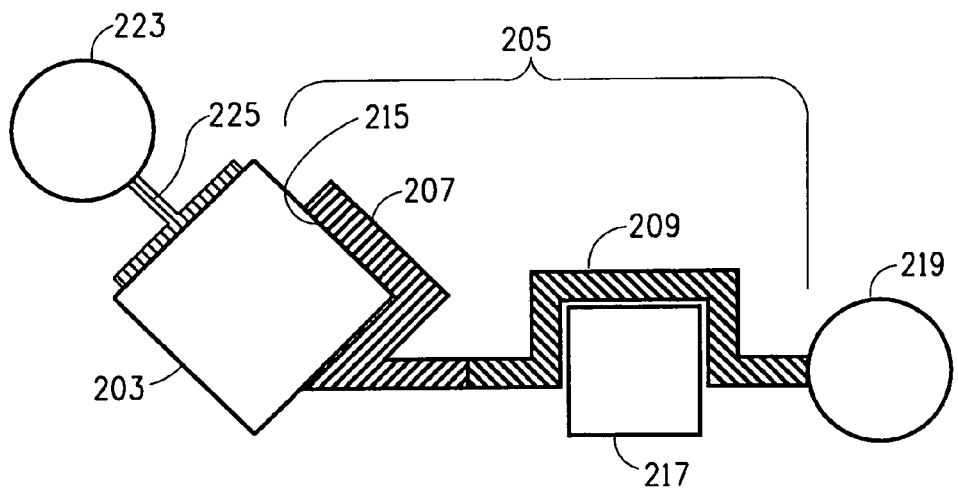
FIG. 3 depicts an embodiment of the present invention as a diblock, optionally bound to a benefit agent at two different positions and/or a target molecule. Also depicted is the optional inclusion of a linker molecule and/or an active domain.

Linker molecules may optionally be used with some embodiments of the present invention for the purpose of attaching the benefit agent to the PMMA-peptide complex (see FIG. 3, reference number 225). Any molecule, compound or complex that will attach the benefit agent to the complex can be used as a linking molecule provided the linking molecule does not contain PMMA or a PMMA-binding domain. The benefit agent may be attached to the complex to either the PMMA moiety or the peptide portion or in the case of a plurality of benefit agent possibly to both. The linking molecules may be designed to bond the benefit agent stably or in the alternative they may be designed to break and release the benefit agent from the complex in a given circumstance. Such circumstances could be, for non-limiting example, a range of pH, a range of temperatures, a range of pressure, while immersed in a certain media, the presence of a particular element, molecule or compound at a certain range of concentration, after a given passage of time, or at a certain average rate for a population of linker molecules.

Specifically the linker may be any of a variety of molecules, such as alkyl chains, phenyl compounds, ethylene glycol, amides, esters and the like. Preferred linkers are hydrophilic and have a chain length from 1 to about 100 atoms, more preferably, from 2 to about 30 atoms. Examples of preferred linkers include, but are not limited to, ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, and ethyl, propyl, hexyl, steryl, cetyl, and palmitoyl alkyl chains. The linker may be covalently attached to the peptide and the benefit agent using any of the coupling chemistries described above. In order to facilitate incorporation of the linker, a bifunctional cross-linking agent that contains a linker and reactive groups at both ends for coupling to the peptide and the benefit agent may be used. Suitable bifunctional cross-linking agents are well known in the art and include, but are not limited to diamines, such as 1,6-diaminohexane; dialdehydes, such as glutaraldehyde; bis N-hydroxysuccinimide esters, such as ethylene glycol-bis(succinic acid N-hydroxysuccinimide ester), disuccinimidyl glutarate, disuccinimidyl suberate, and ethylene glycol-bis(succinimidylsuccinate); diisocyantes, such as hexamethylenediisocyanate; bis oxiranes, such as 1,4 butanediyl diglycidyl ether; dicarboxylic acids, such as succinyldisalicylate; and the like. Heterobifunctional cross-linking agents, which contain a different reactive group at each end, may also be used.

Applications of PMMA Binding Peptides

It will be appreciated by the skilled person that PMMA binding peptides comprising active and target domains having specific functionality may be used in a multiplicity of formats including as delivery means for delivering benefits agents, in assays for diagnostic applications as well as in materials applications for coating PMMA surfaces. The following description of the figures presents a limited number of examples of the method of the invention, but is by no means inclusive of all possible applications and formats.

Referring to FIG. 1 panel A, there is shown a surface 1 comprising, in whole or in part, a PMMA moiety 3. At least some of the PMMA molecules 3 are exposed in various orientations on the exterior of the surface. The PMMA binding peptide 5 comprises at least one, but not limited to one, PMMA binding domain 7. The PMMA binding domain 7 further comprises at least one, but not limited to one, PMMA binding site 15. PMMA binding peptides 5 will bind specifically to PMMA molecules 3, this binding will occur at the PMMA binding site 15 of the PMMA domain 7 within the PMMA binding peptide 5. The PMMA-binding peptide 5 coupled to the PMMA moiety 3 forms a diblock structure. The formation of this diblock structure on a PMMA containing surface 1, such as CORIAN® is useful for coating such surfaces with a protein layer to serve as a sacrificial layer or to mask properties of the surface 1.

FIG. 1 panel B depicts another embodiment of the invention. In this embodiment, a PMMA binding peptide 5 also binds to a surface 1 comprising, in whole or in part, PMMA molecules 3. A benefit agent 19 is coupled to the PMMA binding peptide 5 covalently, ionically or otherwise as described elsewhere herein. Although bound to the PMMA binding peptide 5, the benefit agent 19 generally retains the biological, chemical and physical properties that it exhibited before being coupled to the PMMA binding peptide 5. The complex of the PMMA particle 3, the PMMA-binding peptide 5, and the benefit agent 19 forms a triblock. The proximity of the benefit agent 19 to the surface 1 after binding allows the benefit agent 19 to be active at that location, and provides the chemical property of the benefit agent 19 on the PMMA containing surface 1. Non-limiting examples of the benefit agents 19 are colorants such as dyes and pigments, conditioners, fragrances, pharmaceuticals and the like.

FIG. 1 panel C depicts still another embodiment of the invention. The PMMA binding peptide 5 binds to a surface 1 comprising PMMA 3 as above. Panel C, as in panels A and B, shows the PMMA binding peptide 5 comprising at least one, but not limited to one, PMMA binding domain 7 within its structure. The PMMA binding domain 7 comprises at least one, but not limited to one, PMMA binding site 15. The PMMA binding peptide 5 of panel C further comprises at least one, but not limited to one, active domain 9 different from the PMMA binding domain 7, yet within the same PMMA binding peptide 5. By having an active domain 9 within the peptide 5 and the peptide 5 being bound to a PMMA-containing surface 1 this embodiment of the invention allows the property of the active domain 9 to be transmitted to the surface 1. One non-limiting example of an active domain as exemplified here is a domain having antimicrobial properties.

FIG. 1 panel D depicts still another embodiment of the invention. The PMMA binding peptide 5 binds to a surface 1 comprising PMMA 3 as described above. In this embodiment, the PMMA binding peptide 5 comprises a specific target binding domain 11 targeting other molecules other than PMMA. In this embodiment, the PMMA-binding peptide 1 acts as an intermediary to bring the target molecules close to the surface 1. This may be used to provide the chemical, biologic or physical function of target molecule 17 on the surface 1. However, this embodiment may also be employed to isolate the target molecule 17 from the surrounding media. Another use may be to sample the surrounding media for the presence of the target molecule 17. Non-limiting examples of the other target molecule 17 include benefit agents such as colorants (dyes and pigments) and conditioners as well as biological analytes, (cells, membrane fractions, viral particles, proteins, nucleic acids and the like), body surfaces, (hair, skin, nails, teeth and the like) as well as other organic and inorganic target complexes.

FIG. 1 panel E depicts still another embodiment of the invention. The PMMA binding peptide 5 binds to a surface 1 comprising PMMA 3 as above. Panel E depicts a PMMA binding peptide 5 that contains a linker domain 13 that serves to connect the PMMA binding peptide 5 to a benefit agent 19. The linker domain 13 is a domain that selected to physically separate the benefit agent 19 from the PMMA binding domain(s) 7. Alternatively, although not depicted in the FIG. 1, a single linker domain or many linker domains may be provided to separate various domains within the PMMA-binding peptide. For instance, it may be advantageous to separate the PMMA binding domain from an active domain, or to separate two or more active domains, a linker could be utilized to achieve this separation. The linker domain 13 may simply provide a steric benefit. Although in some uses of this embodiment the linker provides a specific structure or orientation between the PMMA binding peptide 5 and the benefit agent 19 or to limit the conformation of the benefit agent-PMMA binding peptide-PMMA triblock. In other uses of this embodiment the linker 13 provides a flexible region so that the benefit agent-PMMA binding peptide-PMMA triblock can forma particular conformation or a variety of different conformations. Still, in other uses of this embodiment the chemical and physical nature of the linker 13 may be used to change the rheology of the environment surrounding the surface 1 to which the peptide 5 is bound. Non-limiting examples of linker domains 13 that would alter the rheology of the surrounding surface include, hydrophobic, hydrophilic, or charged molecules. Additionally a linker domain 13 may be employed to release a benefit agent 19 from the PMMA-binding peptide 5 under various circumstances. Such circumstances may include for example, a certain range of pH, or a certain range of temperatures, or a certain range of pressures. Such circumstances may also include response to shock, response to the presence of a particular molecule, especially a peptide cleaving molecule, or the passage of time.

Figure 2A:
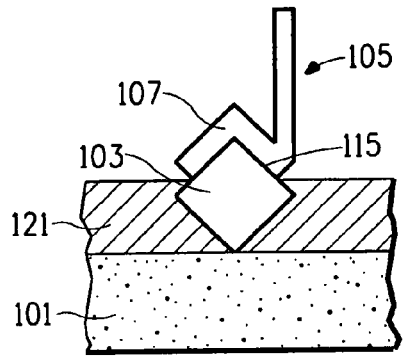
FIG. 2 is a set of panels A-C which depict embodiments of the present invention as they are bound to a PMMA coating containing, in whole or in part, PMMA particles, which is further bound to a surface.
Figure 2B:
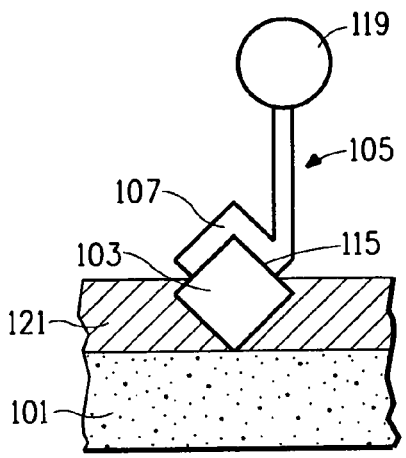
Figure 2C:
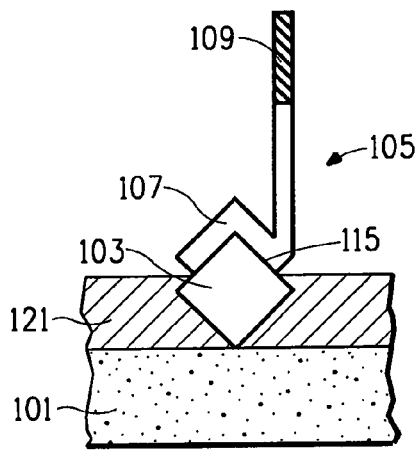

Referring to FIG. 2 panel A, a surface 101 is shown that could be comprised of any surface material. Non-limiting examples of such surfaces are metal, paper, glass and cloth. A coating 121 comprised of in whole or in part, PMMA molecules or moieties 103 has been applied to the surface 101 as shown. In this embodiment of the invention, a PMMA-binding peptide 105 is targeted to the coating. As in the above descriptions the PMMA-binding peptide 105 comprises, in whole or in part, at least one PMMA-binding domain 107, which itself comprises, in whole or in part, at least one PMMA-binding site 115. As described elsewhere herein the PMMA-binding site 115 binds specifically to PMMA molecules 103. In this embodiment the PMMA-binding site 115 binds to exposed portions of PMMA 103 in a PMMA coating 121 on attached to the surface 101. In this embodiment the PMMA-binding peptide 105 is useful to provide an additional coating to PMMA coating 103 already applied to the surface 101. Non-limiting examples of the uses for this embodiment include a sacrificial layer to protect the PMMA coating or in the case of multiple PMMA domains 107 and/or binding sites 115 to act as an adhesive between the PMMA coat 121 and other PMMA moieties 103 or surfaces 101.

Similar to Panel A, FIG. 2 Panel B depicts a PMMA-binding peptide 105 coupled to a PMMA coating 121 on a surface 101. The PMMA-binding peptide 105 depicted in panel B further comprises a benefit agent 119. In this embodiment of the invention, at least one, but not limited to one, benefit agent 119 is coupled to the PMMA-binding peptide 105 by a covalent, ionic or other interactive means. The PMMA binding peptide-benefit agent complex is in turn coupled to a PMMA moiety 103 within the PMMA coating 121 on the surface 101. As described elsewhere herein the benefit agent 119 has some activity or functionally that persists while it is bound to the PMMA-binding peptide 105 and the complex is bound to the PMMA coating 121. The active benefit agent 119 being brought to or near the coating 121 by the PMMA-binding peptide 105 conveys its activity to the coating, modifies the coating or enhances the coating. In a similar embodiment, a plurality of different types of PMMA-binding peptides 105 may be used in combination so that the different benefit agents 119 corresponding to the different PMMA-binding peptides 105 may interact, or act in concert to produce a desirable result.

Similar to Panel A, FIG. 2 Panel C depicts a PMMA-binding peptide 105 bound to a PMMA coating 121 on a surface 101. The PMMA-binding peptide 105 comprises all of the features of the PMMA-binding peptide 105 depicted in Panel A, with the added feature that the peptide includes an active domain 109 separate from the PMMA-binding domain. This active domain 109, remains active as part of the PMMA-binding peptide 105, and further continues to be active when the PMMA-binding peptide 105 binds to PMMA 103 within the PMMA coating 121. The active domain 109, by virtue of being part of the diblock containing the PMMA-binding peptide 105 and the PMMA coating 121, is active in the proximity of the coating 121. This allows the coating 121 to exhibit the activity of the active domain 109 contained in the PMMA-binding peptide 105 bound to the PMMA molecules 103 contained within the coating 121. Additionally, as in panel B, a benefit agent 119 may also be chemically attached to the functional domain containing PMMA-binding peptide 105 (not shown). As stated above, an additional embodiment would be the use of a plurality of different types of PMMA-binding peptides 105 to interact or act in concert to produce a desirable result.

Referring to FIG. 3, another embodiment of the invention is shown in which the PMMA substrate is not bound to a larger surface. In this embodiment the PMMA exists as a PMMA moiety 203 which may be suspended in solution, such as cell growth media, air, water, oil, biological fluids, gels and the like. A PMMA-binding peptide 205 is depicted bound to the PMMA moiety 203. The PMMA-binding'peptide 205 contains within its peptide structure at least one, but not limited to one PMMA binding domain 207. The PMMA binding domain 207 contains within its structure a PMMA binding site 215. PMMA binding domains 207 and PMMA binding sites 215 bind PMMA moieties 203 specifically as described elsewhere herein. Binding of the PMMA-binding peptide 205 to the PMMA 203 occurs at the PMMA binding site 215 with the PMMA binding domain 207. The binding of PMMA moieties 203 to the PMMA-binding peptide 205 forms a diblock structure.

Other embodiments of the invention add additional elements to the di-block formation of PMMA moiety 203 and PMMA-binding peptide 205. One such embodiment, involves binding a benefit agent 219 to the PMMA-binding peptide 205. The addition of a benefit agent 219 to the diblock structure forms a triblock structure. The benefit agent 219 may be coupled to the PMMA-binding peptide 205 by any known means, as described above. The function of benefit agents 219 is discussed in greater detail elsewhere herein.

Alternatively the benefit agent 223 may be attached to the PMMA moiety 203. In this format, the benefit agent 223 is attached to the PMMA moiety or bead 203 typically by chemical means or bonds 225. The bond may be part of the benefit agent 223 or may be an independent structure that is bound to the PMMA 203 for the purpose of binding the benefit agent 223. In the alternative, the bond structure 225 may be bound to the benefit agent 223 for the purpose of binding it to the PMMA 203. The binding structure 225 may be a permanent bond, but in some forms of the embodiment may be easily broken under certain conditions. In other forms of the embodiment, the bond 225 may allow the benefit agent 223 to be leached from the PMMA moiety or bead 203 under certain conditions. In still other forms of the embodiment, the bond 225 may allow the benefit agent 223 to be released over time at regular or specific time intervals. Alternatively, the bond 225 itself may be in whole or in part be composed of PMMA. In this way, the PMMA moiety or bead 203 may be in whole or in part the binding structure 225. The benefit agent 223 may be partially or fully embedded with the PMMA moiety or bead 203.

In another embodiment described by FIG. 3, the PMMA-binding peptide 205 is bound the PMMA 203 as described above and the complex may optionally be bound to a benefit agent 219 and/or 223 by any method described elsewhere herein. The additional feature of this embodiment is at least one or a plurality of additional active peptide domains 209 within the PMMA-binding peptide 205. Any known peptide active domain 209 can be used in this embodiment. Alternatively, the active domain 209 may be a linker domain or may function as a target domain and bind a target 217.

Figure 4:
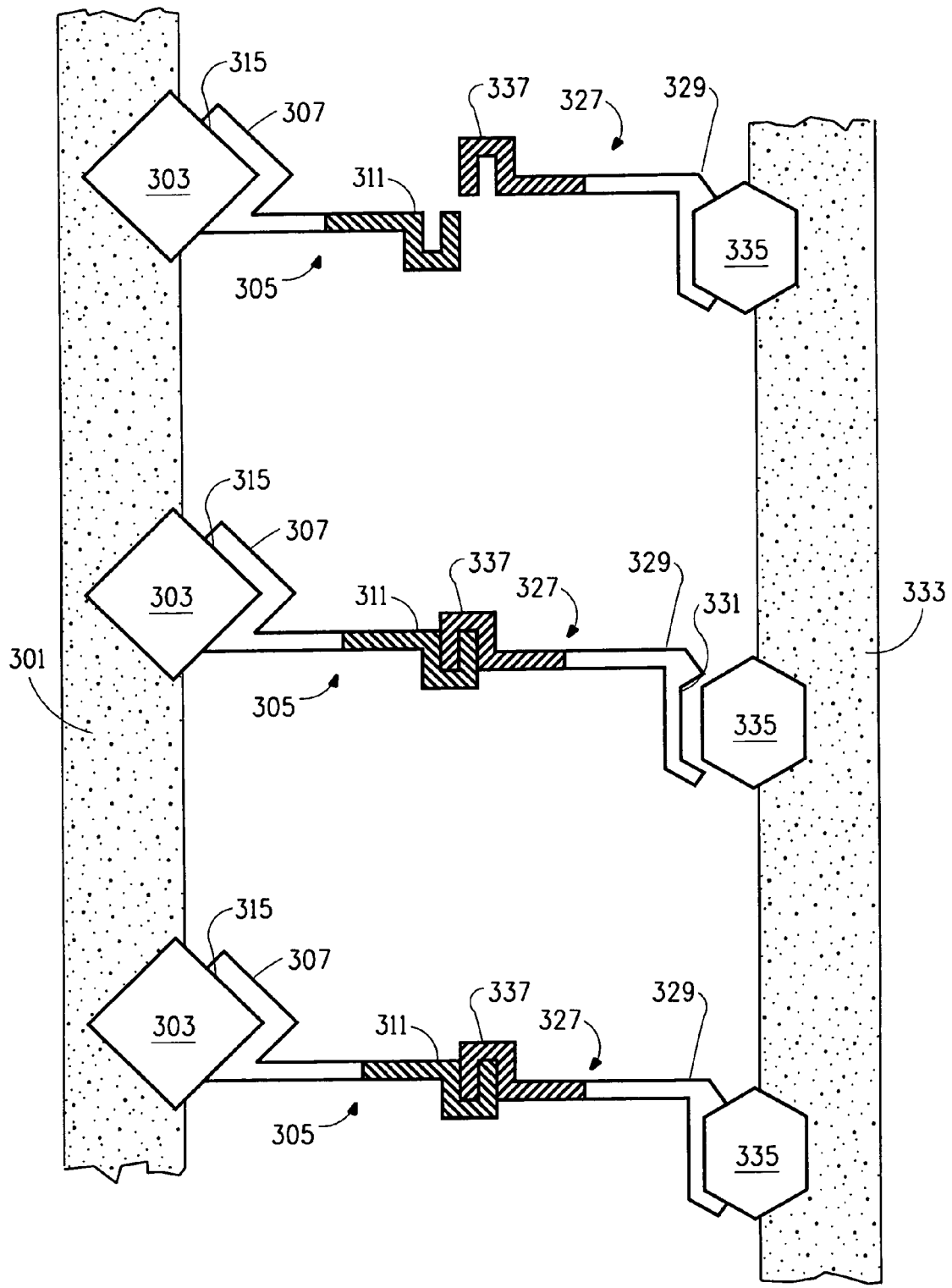
FIG. 4 depicts an embodiment of the present invention used to bond a PMMA containing surface with another surface which may contain PMMA or another known target molecule.
Figure 5:
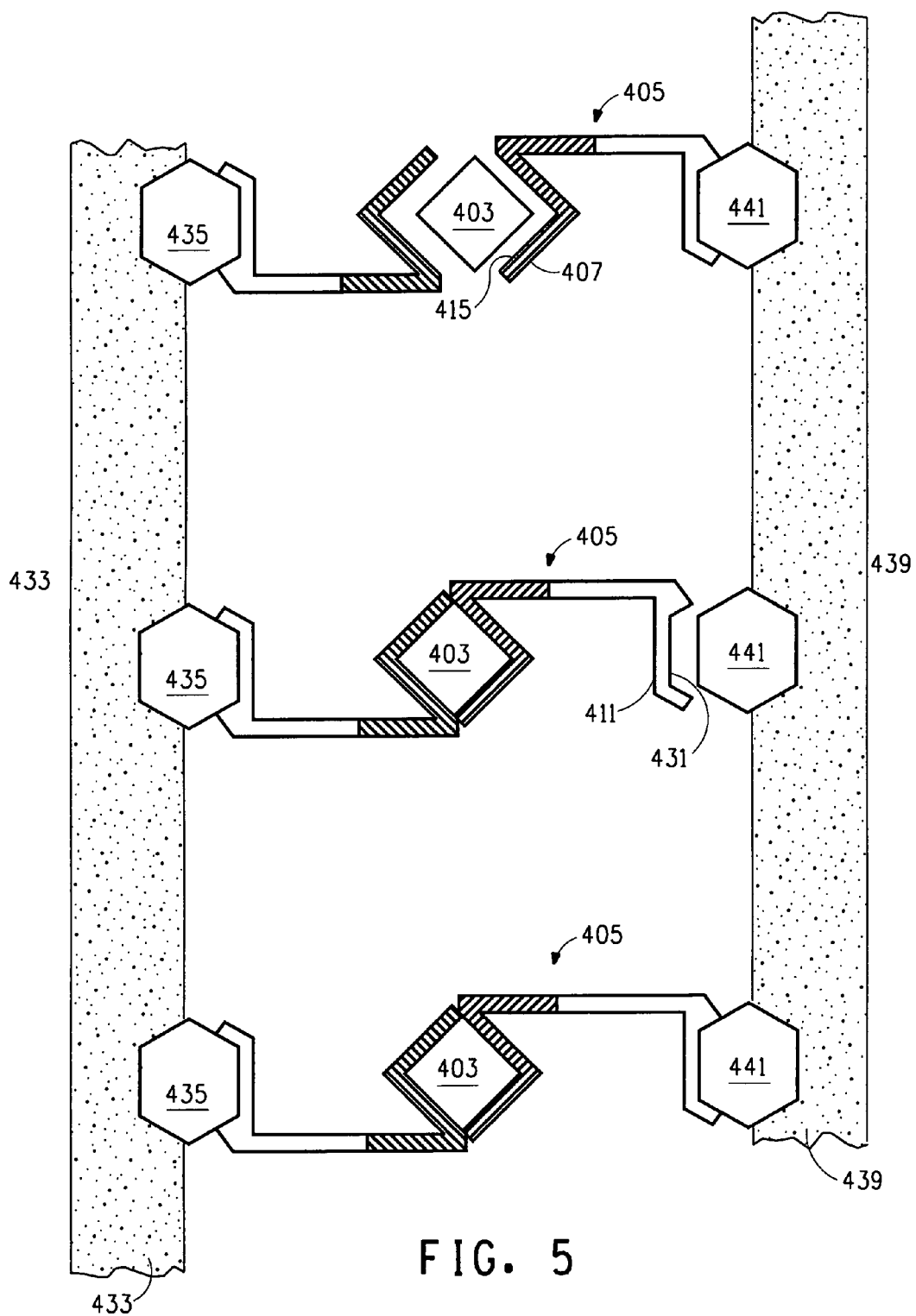
FIG. 5 depicts an embodiment of the present invention used to bond to surfaces together wherein neither necessarily contains PMMA.
Figure 6A:
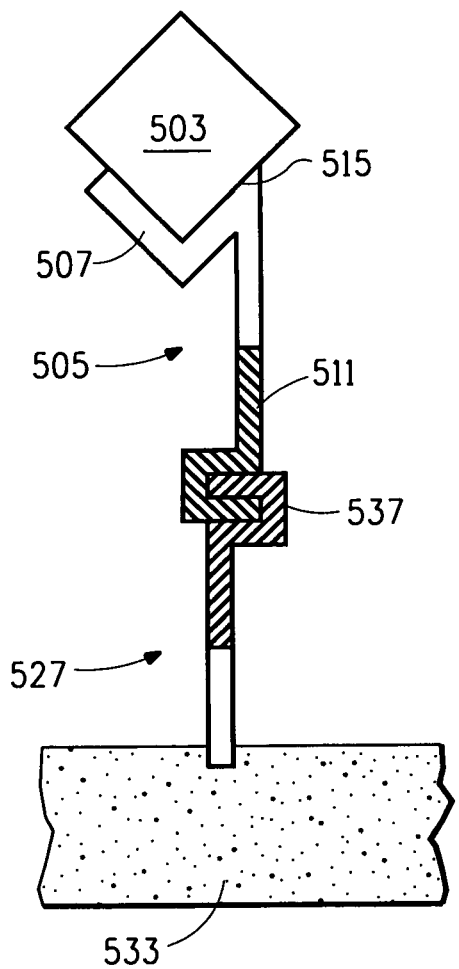
FIG. 6 is a set of panels A-D which depict embodiments of the present invention used to coat a surface with PMMA.
Figure 6B:
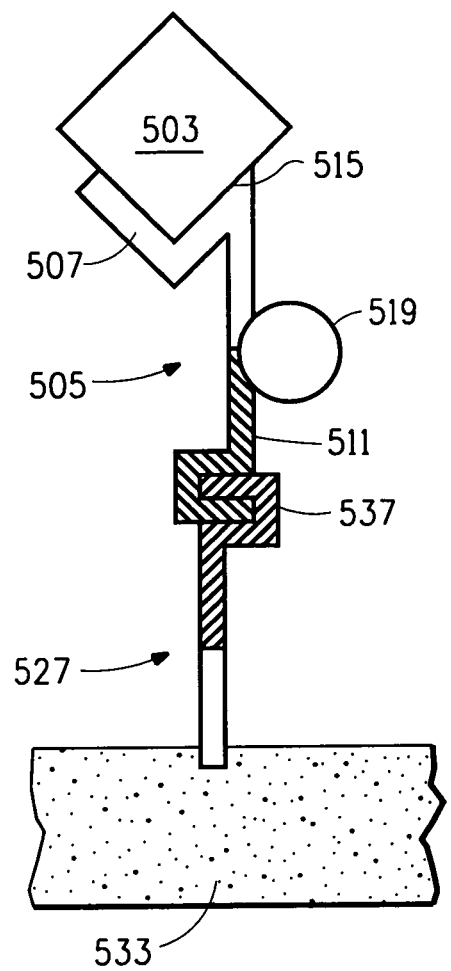
Figure 6C:
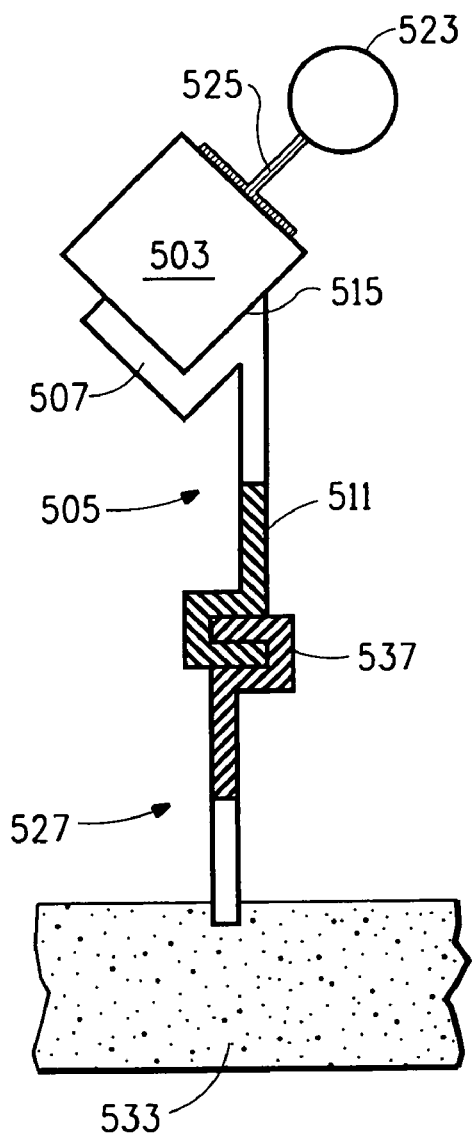
Figure 6D:
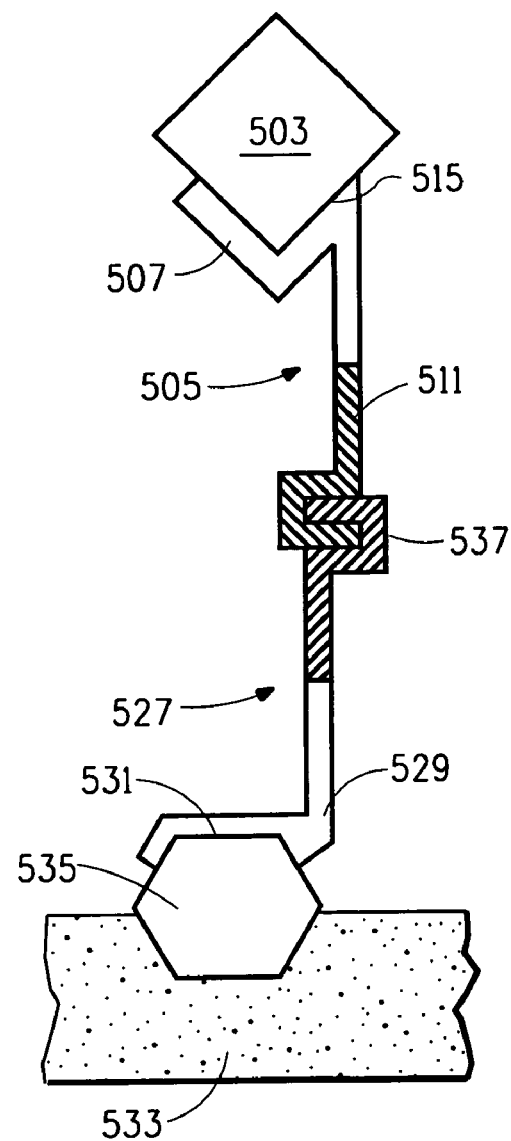

Additional embodiments of the invention are illustrated in FIGS. 4 and 5. Referring to FIGS. 4 and 5, a plurality of PMMA-binding peptides 305 may be employed to bring substances together. FIG. 4 depicts a PMMA-binding peptide 305 used to bring a PMMA containing surface 301 together with another surface 333. The PMMA containing surface 301 is comprised in whole or in part of PMMA moieties 303 At least some PMMA moieties 303 are exposed in part or in full on the at least one side of the surface 301. Likewise, the non-PMMA surface or complementary surface 333, is comprised in whole or in part of a known moiety 335 for which there exists a peptide binding-domain 329 or for which a peptide binding domain 329 can be designed using the methods described elsewhere herein. The amino acid structure of the PMMA-binding peptides 305 comprises in whole or in part of at least one PMMA binding domain 307, but possibly more than one. The PMMA binding domain 307 itself comprises at least one or a plurality of PMMA binding sites 315. PMMA binding sites 315 are able to bind to the exposed PMMA 303 of the PMMA containing surface 301 and in such way to adhere the PMMA-binding peptides 305 to surface 301. In addition to comprising one or more PMMA binding domains 307, the PMMA-binding peptide 305 of this embodiment also comprises at least one, but possibly more, target binding domains 311. The target binding domain 311 specifically binds another target domain 337 in a handshake fashion allowing the complex to serve as an adhesive binding the PMMA and non-PMMA containing surfaces together. The target binding domain 311 in some uses may be capable of binding to itself. In that case, the target binding domain 311 and the target domain 337 could be identical.

The complementary surface 333 is composed a known surface-exposed moiety or a complementary moiety 335, for which there is a known peptide binding domain 329, a complementary peptide binding domain 329. A complementary moiety binding peptide 327 is composed of at least one, but possibly more than one, complementary moiety binding domain 329, which itself is composed of at least one but possibly more than one complementary moiety binding site 331. The complementary moiety binding site 331 binds specifically to complementary moieties 335 exposed on the complementary surface 333. The complementary moiety binding peptide 327 is bound to the complementary surface 333 because it is composed of at least one complementary moiety binding domain 329 which contains at least one complementary moiety binding site 331. In addition to the complementary moiety binding domain 329, the complementary moiety binding peptide 327 also contains at least one but possibly more than one target domain 337. As discussed above, the target binding domain 311 of the PMMA-binding peptide 305 binds to the target domain 337.

It should be clear to one skilled in the art that the complementary surface 333 may be composed of PMMA itself and the complementary moiety binding domain 327 could be a PMMA binding domain. This embodiment is useful because it provides an adhesive that is specific and functional even in adverse circumstances among such circumstances, as not limiting examples, are the presence of water, oil, or dirt.

FIG. 5 depicts another embodiment of the invention useful for binding two surfaces together. In this embodiment neither surface needs to necessarily contain PMMA, although that possibility is not excluded. The primary structure of the peptide based adhesive is similar to that shown in FIG. 4. Two surfaces are provided 433, 439. Each surface comprising a target molecule 435, 441 either of which may or may not be the same and may or not be PMMA. A peptide diblock is provided comprising in each case a target binding peptide 405 with a target binding domain 411 comprising a target binding site 431. The target binding peptide 405 comprises a PMMA binding domain 407 having a PMMA binding site 415, useful for binding PMMA moieties. Juxtaposing of the two surfaces in the presence of PMMA moieties 403 results in adhesion of the surfaces though the PMMA.

It will be apparent to the skilled person that this embodiment may also be practiced with the addition of a benefit agent(s) and/or peptide domain(s) as describe above. This embodiment is useful because it provides an adhesive that is specific and functional even in adverse circumstances among such circumstances, as not limiting examples, are the presence of water, oil, or dirt.

FIG. 6 depicts an embodiment of the invention in which a surface 533 may be coated with PMMA 503 using PMMA-binding peptide 505 containing a target binding domain 511. FIG. 6 panel A depicts a surface 533 coated with a target peptide 527 that contains in part or whole a target domain 537. The target peptide 527 may be applied to the surface 533 by any method either described herein or known in the art; one method will be described in detail later when discussing FIG. 6 panel D. The PMMA-binding peptides 505 used in this embodiment each contain, as described above, at least one PMMA binding domain 507 which in turn contains at least one PMMA binding site 515. The PMMA binding site 515 binds PMMA 503 specifically as described elsewhere herein. In addition to the PMMA binding domain 507, the PMMA-binding peptides 505 also each contain at least one but possibly more than one target binding domain 511. The target binding domain used is selected, or created, using methods described or known, to bind specifically to the target domain 537 of the target peptide 527 on the surface 533. If the PMMA-binding peptide 505 and PMMA moieties 503 as described are allowed to move freely in a medium around the exposed surface 533, PMMA-binding peptide 505 will adhere to the peptides 527 on the surface 533 through the bonding of the target binding domain 511 of the PMMA-binding peptide 505 to the target domain 537 of the surface peptide 527. PMMA moieties in the media will bind to the PMMA binding site 515 of the PMMA binding domain 507 of the PMMA-binding peptide 505 forming a diblock structure. With PMMA 503 bound to the PMMA-binding peptide 505 and it in turn bound to the suface peptides 527 that are bound to the surface 533, PMMA 503 moieties will coat the surface 533.

FIG. 6 panel B, depicts the same interactions of PMMA-binding peptide 505, PMMA 503 and a peptide coated surface 533, as described in panel A, with the addition of a benefit agent 517 coupled to the PMMA-binding peptide 505 which itself contains at least one target binding domain 511. Using methods described herein this embodiment couples a benefit agent 517 to the PMMA-binding peptide 505. When the complex of the benefit agent 517 and the PMMA-binding peptide 505 bind a PMMA moiety 503 a triblock is formed. The triblock structure does not prevent the benefit agent 517 from being functionally active or from the target binding domain 511 from binding the target peptide 527. The addition of a benefit agent 517 to the PMMA-binding peptide 505 allows the surface to be coated with both a benefit agent 519 and PMMA moieties 503. Non-limiting examples of benefits agents 517 that may be used with this embodiment are dyes, colorants, antimicrobials, and stain repelling moieties.

FIG. 6 panel C, depicts the same interactions as in panel A, and provides the addition of a benefit agent 523 bound to PMMA. In this embodiment, the benefit agent 523 is attached to the PMMA moiety or bead 503 with a bond structure 525. The bonding structure may be part of the benefit agent 523 or may be an independent structure that is bound to the PMMA 503 for the purpose of binding the benefit agent 523. Or in the alternative, the bond structure 525 may be bound to the benefit agent 523 for the purpose of binding it to the PMMA 503. The binding structure 523 may be a permanent bond, but in some forms of the embodiment may be easily broken under certain conditions. In other forms of the embodiment the binding structure 525 may allow the benefit agent 523 to be leached from the PMMA 503 under certain conditions. In still other forms of the embodiment the binding structure might allow the benefit agent 523 to be released over time at regular or specific time intervals. In an alternative form of this embodiment the binding structure 525 itself may be in whole or in part be composed of PMMA. In this form, the PMMA 503 may be in whole or in part the binding structure 525. The benefit agent 523 may be partially or fully embedded with the PMMA 503. A triblock structure is formed when the benefit agent 523 coupled to the PMMA moiety 503 that is inturn bound to the PMMA-binding peptide 505. The triblock structure is capable of binding the target peptide as described above.

FIG. 6 panel D, Depicts a PMMA-binding peptide 505 and PMMA moiety or bead 503 similar to the PMMA-binding peptide 505 described in panel A. In this embodiment, the target peptide 527 depicted is not attached directly to the surface 533. The target peptide 527 contains a target binding domain 537 as in panels A, B, and C and additionally contains a surface moiety binding domain 529. The surface moiety binding domain 529 is selected to bind specifically to a known moiety that is known to be exposed on the surface 533. The surface binding moiety domain 529 contains at least one, but possibly more than one, surface moiety bind site 531. The surface moiety binding site 531 is the point of attachment between the surface moiety 535 and the surface moiety binding domain 529. Through the interaction of the surface moiety binding domain 529 and the surface moiety 535 the PMMA-binding peptide 505 is attached to the surface 533. Further through the binding interaction of the PMMA moieties or beads 503 and PMMA-binding peptide 505 bound to the surface 503, the surface 503 is coated with PMMA moieties or beads 503.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "sec" means second(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "mg" means milligram(s), "g" means the gravitation constant, "rpm" means revolutions per minute, "pfu" means plague forming unit, "BSA" means bovine serum albumin, "ELISA" means enzyme linked immunosorbent assay, "IPTG" means isopropyl β-D-thiogalactopyranoside, "A" means absorbance, "$A_{450}$" means the absorbance measured at a wavelength of 450 nm, "TBS" means Tris-buffered saline, "TBST-X" means Tris-buffered saline containing Tween® 20 where "X" is the weight percent of Tween® 20, "Xgal" means 5-bromo-4-chloro-3-indolyl-beta-D-galactopyranoside, "SEM" means standard error of the mean, "vol %" means volume percent.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989.

All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Example 1

Selection of Polymethylmethacrylate (PMMA)-Binding Peptides Using Biopanning

The purpose of this Example was to identify phage peptides that bind to polymethylmethacrylate (PMMA) using a modified phage display biopanning method.

Phage Display Peptide Libraries:

The phage libraries used in the present invention, Ph.D.-12™ Phage Display Peptide Library Kit and Ph.D.-7™ Phage Display Library Kit, were purchased from New England BioLabs (Beverly, Mass.). These kits are based on a combinatorial library of random peptide 7 or 12-mers fused to a minor coat protein (pIII) of M13 phage. The displayed peptide is expressed at the N-terminus of pIII, such that after the signal peptide is cleaved, the first residue of the coat protein is the first residue of the displayed peptide. The Ph.D.-7 and Ph.D.-12 libraries consist of approximately $2.8 \times 10^9$ and $2.7 \times 10^9$ sequences, respectively. A volume of 10 µL contains about 55 copies of each peptide sequence. Each initial round of experiments was carried out using the original library provided by the manufacturer in order to avoid introducing any bias into the results.

Biopanning Against a PMMA Surface:

The PMMA materials used were ⅛ inch (32 mm) thick, ½ inch (12.7 mm) diameter disks of Lucite® sheet (obtained from E.I. du Pont de Nemours and Co., Wilmington, Del.) and a dot blot apparatus (obtained from Schleicher & Schuell, Keene, N.H.). The following protocol was used for biopanning against the PMMA disk. The PMMA disk was placed in a tube filled with 5 mL of 90% isopropanol for 30 min at room temperature and then washed 5 times for 10 min each with deionized water. Then, 5 mL of blocking buffer consisting of 1 mg/mL BSA in TBST containing 0.5% Tween® 20 (TBST-0.5%) was added to the tube and incubated for 1 h at 4° C.

The disk was washed 5 times with TBST-0.5% and then 2 mL of TBST-0.5% containing 1 mg/mL BSA was added to each well. Then, 10 µL of the original phage library ($2 \times 10^{11}$ pfu), either the 12-mer or 7-mer library, was added to the disk and incubated for 15 min at room temperature. The disk was washed 10 times with TBST-0.5%. The disk was then transferred to a clean tube, 2 mL of a non-specific elution buffer consisting of 1 mg/mL BSA in 0.2 M glycine-HCl, pH 2.2, was added to the tube and incubated for 10 min. The disk was washed three more times with the elution buffer and then washed three times with TBST-0.5%. The disk, which had acid resistant phage peptides still attached, was used to directly infect the host cells E. coli ER 2738 (New England BioLabs, Beverly, Mass.), for phage amplifications. The disk was incubated with an overnight E. coli ER2738 culture diluted 1:100 in LB medium, at 37° C. for 4.5 h. After this time, the cell culture was centrifuged for 30 s and the upper 80% of the supernatant was transferred to a fresh tube, ⅙ volume of PEG/NaCl (20% polyethylene glycol-800, obtained from Sigma Chemical Co. St. Louis, Mo., 2.5 M sodium chloride) was added, and the phage was allowed to precipitate overnight at 4° C. The precipitate was collected by centrifugation at 10,000×g at 4° C. and the resulting pellet was resuspended in 1 mL of TBS. This was the first round of amplified stock. The amplified first round phage stock was then titered according to the method described below. For the next round of biopanning, more than $2 \times 10^{11}$ pfu of phage stock from the first round was used. The biopanning process was repeated for 3 to 4 rounds depending on the experiments.

After the acid wash steps in the final round of biopanning, the PMMA disk was used to directly infect 500 µL of mid-log phase bacterial host cells, E. coli ER2738, which were then grown in LB medium for 20 min and then mixed with 3 mL of agarose top (LB medium with 5 mM $MgCl_2$, and 0.7% agarose) at 45° C. This mixture was spread onto a LB medium/IPTG/S-Gal™ plate (LB medium with 15 g/L agar, 0.05 g/L IPTG, and 0.04 g/L S-Gal™) and incubated overnight at 37° C. The black plaques were counted to calculate the phage titer. The single black plaques were randomly picked for DNA isolation and sequencing analysis. The amino acid sequences of these high affinity, PMMA-binding phage peptides are given in Table 7.

TABLE 7

Amino Acid Sequences of High Affinity PMMA-Binding Phage Peptides from the 7- and 12-Mer Libraries

| Clone ID | Amino Acid Sequence | SEQ ID NO: |
|---|---|---|
| A09 | IPWWNIRAPLNA | 1 |
| D09 | TAVMNVVNNQLS | 2 |
| A03 | VPWWAPSKLSMQ | 3 |
| A06 | MVMAPHTPRARS | 4 |
| B04 | TYPNWAHLLSHY | 5 |
| B09 | TPWWRIT | 6 |
| B01 | DLTLPFH | 7 |
| PB411 | GTSIPAM | 8 |
| P307 | HHKHVVA | 9 |
| P410 | HHHKHFM | 10 |
| P202 | HHHRHQG | 11 |
| PNM407 | HHWHAPR | 12 |

Example 2

Characterization of PMMA-Binding Phage Peptide Clones by ELISA

Enzyme-linked immunosorbent assay (ELISA) was used to evaluate the PMMA-binding affinity of the selected phage-peptide clones identified in Example 1 along with a skin-1 phage clone TPFHSPENAPGS (given as SEQ ID NO:81), which served as a control.

An empty 96-well apparatus, a Minifold I Dot-Blot System from Schleicher & Schuell, Inc. (Keene, N.H.) was used as the PMMA surface. For each clone to be tested, the well was incubated for 1 h at room temperature with 200 µL of blocking buffer, consisting of 2% non-fat dry milk in TBS. The blocking buffer was removed by inverting the systems and blotting them dry with paper towels. The wells were rinsed 6 times with wash buffer consisting of TBST-0.5%. The wells were filled with 200 µL of TBST-0.5% containing 1 mg/mL BSA and then 10 µL (over $10^{12}$ copies) of purified phage stock was added to each well. The samples were incubated at 37° C. for 15 min with slow shaking. The non-binding phage was removed by washing the wells 10 to 20 times with TBST-0.5%. Then, 100 µL of horseradish peroxidase/anti-M13 antibody conjugate (Amersham USA, Piscataway, N.J.), diluted 1:500 in the blocking buffer, was added to each well and incubated for 1 h at room temperature. The conjugate solution was removed and the wells were washed 6 times with TBST-0.05%. TMB substrate (200 µL), obtained from Pierce Biotechnology (Rockford, Ill.) was added to each well and the color was allowed to develop for between 5 to 30 min, typically for 10 min, at room temperature. Then, stop solution (200 µL of 2 M $H_2SO_4$) was added to each well and the solution was transferred to a 96-well plate and the $A_{450}$ was measured using a microplate spectrophotometer (Molecular Devices, Sunnyvale, Calif.). The resulting absorbance values, reported as the mean of at least three replicates, and the standard error of the mean (SEM) are given in Table 8.

TABLE 8

Results of ELISA Assay

| Clone ID | SEQ ID NO: | PMMA $A_{450}$ | SEM |
|---|---|---|---|
| Skin-1 (Control) | 81 | 0.127 | 0.057 |
| A09 | 1 | 2.227 | 0.020 |
| D09 | 2 | 2.037 | 0.057 |
| A03 | 3 | 0.762 | 0.081 |
| A06 | 4 | 2.09 | 0.115 |
| B04 | 5 | 2.095 | 0.065 |
| B09 | 6 | 2.261 | 0.016 |
| B01 | 7 | 2.112 | 0.060 |

The results demonstrate that all of the PMMA-binding phage peptides tested had a significantly higher binding affinity for PMMA than the control skin-1 peptide.

Example 3

Determination of the PMMA-Binding Affinity of PMMA-Binding Peptides

The purpose of this Example was to determine the affinity of the PMMA-binding peptides for PMMA surfaces, measured as $MB_{50}$ values, using an ELISA assay. The term "$MB_{50}$" refers to the concentration of the binding peptide that gives a signal that is 50% of the maximum signal obtained in an ELISA-based binding assay. The $MB_{50}$ provides an indication of the strength of the binding interaction or affinity of the components of the complex. The lower the value of $MB_{50}$, the stronger the interaction of the peptide with the PMMA substrate.

PMMA-binding peptide A09 (SEQ ID NO:1) was synthesized by Synpep Inc. (Dublin, Calif.). The peptide was biotinylated by adding a biotinylated lysine residue at the C-terminus of the amino acid binding sequence for detection purposes and an amidated cysteine was added to the C-terminus of the sequence.

$MB_{50}$ Measurement of PMMA-Binding Peptide A09:

The $MB_{50}$ measurements of biotinylated peptide binding to PMMA were done using the 96-well apparatus described in Example 2. The 96-wells were blocked with blocking buffer (SuperBlock™ from Pierce Chemical Co., Rockford, Ill.) at room temperature for 1 h, followed by six washes with TBST-0.5%, 2 min each, at room temperature. Various concentrations of biotinylated, binding peptide were added to each well, incubated for 15 min at 37° C., and washed six times with TBST-0.5%, 2 min each, at room temperature. Then, streptavidin-horseradish peroxidase (HRP) conjugate (Pierce Chemical Co., Rockford, Ill.) was added to each well (1.0 µg per well), and incubated for 1 h at room temperature. After the incubation, the wells were washed six times with TBST-0.5%, 2 min each at room temperature. Finally, the color development and the absorbance measurements were performed as described in Example 2.

The results were plotted as $A_{450}$ versus the concentration of peptide using GraphPad Prism 4.0 (GraphPad Software, Inc., San Diego, Calif.). The $MB_{50}$ values were calculated from Scatchard plots and are shown Table 9.

$MB_{50}$ Measurement of Tetramer PMMA-Binding Peptide A09:

For the $MB_{50}$ measurement of the peptide A09 tetramer, the PMMA surface and all the binding conditions were the same as described above. The tetrameric-A09 peptide complex was prepared by mixing streptavidin-HRP and biotinylated peptide A09 in a 1:4 molar ratio. After all the blocking and washing steps, various concentrations of Streptavidin/$(A09)_4$ complex were added to each well, incubated for 15 min at 37° C., and washed six times with TBST-0.5%, 2 min each, at room temperature. Then, color development and the absorbance measurements were performed as described in Example 2. The results were plotted as $A_{450}$ versus the concentration of peptide complex using GraphPad Prism 4.0 (GraphPad Software, Inc., San Diego, Calif.). The $MB_{50}$ values were calculated from Scatchard plots and are shown in Table 9.

TABLE 9

Summary of $MB_{50}$ Values for PMMA-Binding Peptides

| Binding Peptide | Substrate | $MB_{50}$, M |
|---|---|---|
| A09 | PMMA | $5.9 \times 10^{-8}$ |
| Streptavidin/$(A09)_4$ | PMMA | $3.9 \times 10^{-9}$ |

The results demonstrate that the binding affinity of the PMMA-binding peptide, A09, and the straptavidin/A09 tetramer complex for PMMA was high. The use of multiple copies of the binding peptide in the A09 tetramer complex increased the binding affinity by more than 10-fold.

What is claimed is:

1. A method for delivering a functional peptide to a PMMA ("polymethyl methacrylate") surface comprising, a) providing a peptide reagent having a general structure selected from the group consisting of:

$PMMA_m\text{-}(PmBP)_n$;  A)

$PMMA_m\text{-}(PmBP\text{-}BAp)_n$;  B)

$PMMA_m\text{-}(PmBP\text{-}AD)_n$;  C)

$PMMA_m\text{-}(PmBP\text{-}TBD)_n$;  D)

$PMMA_m\text{-}(PmBP\text{-}L\text{-}BA)_n$; and  E)

$PMMA_m\text{-}[(PmBP)_q\text{-}(L)_x\text{-}(PmBP)_r]_n\text{-}L\text{-}BA$;  F)

wherein:

i) PMMA is a polymethylmethacrylate moiety ii) PmBP is a PMMA binding peptide having a PMMA binding domain;

iii) BA is at least one benefit agent;

iv) AD is at least one active domain incorporated into a PMMA binding peptide;

v) TBD is at least one target binding domain incorporated into a PMMA binding peptide;

vi) L is a linker molecule;

vii) m=the number of PMMA moieties available for binding;

viii) n=is less than m;

xi) p=1-20;

x) x=1-20; and xi) r=1-50;

b) providing a PMMA$_m$ surface; and
c) contacting the peptide reagent of (a) with the PMMA$_m$ surface of (b) under conditions whereby PmBP binds to the PMMA$_m$ surface.

2. A method for delivering a benefit agent to a PMMA$_m$ substrate comprising:
a) providing a peptide reagent comprising a PMMA$_m$-binding peptide ("PmBP") having the general structure selected from the group consisting of:

PMMA$_m$-(PmBP-BAp)$_n$;     A)

PMMA$_m$-(PmBP-L-BA)$_n$; and     B)

PMMA$_m$-[(PmBP)$_q$-(L)$_x$-(PmBP)$_r$]$_n$-L-BA;     C)

wherein:
i) PMMA is a polymethacrylate moiety
ii) PmBP is a PMMA binding peptide having a PMMA binding domain;
iii) BA is at least one benefit agent;
vi) L is a linker molecule;
vii) m=the number of PMMA moieties available for binding;
viii) n=is less than or equal to m;
xi) p=1-20;
x) x=1-20; and
xi) r=1-50;
b) providing a PMMA$_m$ substrate; and
c) contacting the peptide reagent of (a) with the substrate of (b) under conditions whereby the PmBP binds to the PMMA substrate.

3. The method according to claim 2 wherein the at least one benefit agent is selected from the group consisting of pharmaceuticals, markers, colorants, conditioners and fragrances.

4. A method for preparing a PMMA surface coated with one or more peptide reagents comprising:

a) providing a peptide reagent according to a general structure selected from the group consisting of:

PMMA$_m$-(PmBP)$_n$;     A)

PMMA$_m$-(PmBP-BAp)$_n$;     B)

PMMA$_m$-(PmBP-AD)$_n$;     C)

PMMA$_m$-(PmBP-TBD)$_n$;     D)

PMMA$_m$-(PmBP-L-BA)$_n$; and     E)

PMMA$_m$-[(PmBP)$_q$-(L)$_x$-(PmBP)$_r$]$_n$-L-BA;     F)

wherein:
i) PMMA is a polymethylmacrylate moiety
ii) PmBP is a PMMA binding peptide having a PMMA binding domain;
iii) BA is at least one benefit agent;
iv) AD is at least one active domain incorporated into a PMMA binding peptide;
v) TBD is at least one target binding domain incorporated into a PMMA binding peptide;
vi) L is a linker molecule;
vii) m=the number of PMMA moieties available for binding;
viii) n=is less than or equal to m;
xi) p=1-20;
x) x=1-20;
xi) r=1-50;
and
b) contacting the peptide reagent of (a) with a PMMA surface under conditions whereby the peptide reagent binds to the PMMA surface.

* * * * *

SEQUENCE LISTING

<160> NUMBER OF SEQ ID NOS: 179

<210> SEQ ID NO 1
<211> LENGTH: 12
<212> TYPE: PRT
<213> ORGANISM: Artificial sequence
<220> FEATURE:
<223> OTHER INFORMATION: Polymethylmethacrylate binding peptides

<400> SEQUENCE: 1

Ile Pro Trp Trp Asn Ile Arg Ala Pro Leu Asn Ala
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 2

Thr Ala Val Met Asn Val Val Asn Asn Gln Leu Ser
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Polymethylmethacrylate-binding peptide

```
<400> SEQUENCE: 3

Val Pro Trp Trp Ala Pro Ser Lys Leu Ser Met Gln
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 4

Met Val Met Ala Pro His Thr Pro Arg Ala Arg Ser
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 5

Thr Tyr Pro Asn Trp Ala His Leu Leu Ser His Tyr
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 6

Thr Pro Trp Trp Arg Ile Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 7

Asp Leu Thr Leu Pro Phe His
1               5

<210> SEQ ID NO 8
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 8

Gly Thr Ser Ile Pro Ala Met
1               5

<210> SEQ ID NO 9
<211> LENGTH: 7
<212> TYPE: PRT
<213> ORGANISM: Artificial Sequence
<220> FEATURE:
<223> OTHER INFORMATION: Polymethylmethacrylate-binding peptide
```

```
<400> SEQUENCE: 9

His His Lys His Val Val Ala
1               5

<210> SEQ ID NO 10
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 10

His His His Lys His Phe Met
1               5

<210> SEQ ID NO 11
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 11

His His His Arg His Gln Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 12

His His Trp His Ala Pro Arg
1               5

<210> SEQ ID NO 13
<211> LENGTH: 17
<212> TYPE: PRT
<213> ORGANISM: Artificial sequence
<220> FEATURE:
<223> OTHER INFORMATION: antimicrobial peptide sequence

<400> SEQUENCE: 13

Pro Lys Gly Leu Lys Lys Leu Leu Lys Gly Leu Lys Lys Leu Leu Lys
1               5                   10                  15

Leu

<210> SEQ ID NO 14
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 14

Lys Gly Leu Lys Lys Leu Leu Lys Gly Leu Lys Lys Leu Leu Lys Leu
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Antimicrobial peptide sequence
```

<400> SEQUENCE: 15

Lys Gly Leu Lys Lys Leu Leu Lys Leu Lys Lys Leu Leu Lys Leu
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 16

Leu Lys Lys Leu Leu Lys Leu Leu Lys Lys Leu Leu Lys Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Antimicrobial peptide sequence

<400> SEQUENCE: 17

Leu Lys Lys Leu Leu Lys Leu Leu Lys Lys Leu Leu
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Antimicrobial peptide sequences

<400> SEQUENCE: 18

Val Ala Lys Lys Leu Ala Lys Leu Ala Lys Lys Leu Ala Lys Leu Ala
1               5                   10                  15

Leu

<210> SEQ ID NO 19
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 19

Phe Ala Lys Leu Leu Ala Lys Ala Leu Lys Lys Leu Leu
1               5                   10

<210> SEQ ID NO 20
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 20

Lys Gly Leu Lys Lys Gly Leu Lys Leu Leu Lys Lys Leu Leu Lys Leu
1               5                   10                  15

<210> SEQ ID NO 21
<211> LENGTH: 16
<212> TYPE: PRT
<213> ORGANISM: Artificial Sequence
<220> FEATURE:

<223> OTHER INFORMATION: Antimicrobial peptide sequence

<400> SEQUENCE: 21

Lys Gly Leu Lys Lys Leu Leu Lys Leu Gly Lys Lys Leu Leu Lys Leu
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 22

Lys Gly Leu Lys Lys Leu Gly Lys Leu Leu Lys Lys Leu Leu Lys Leu
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 23

Lys Gly Leu Lys Lys Leu Leu Lys Leu Leu Lys Lys Gly Leu Lys Leu
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 24

Lys Gly Leu Lys Lys Leu Leu Lys Leu Leu Lys Lys Leu Gly Lys Leu
1               5                   10                  15

<210> SEQ ID NO 25
<211> LENGTH: 19
<212> TYPE: PRT
<213> ORGANISM: Artificial Sequence
<220> FEATURE:
<223> OTHER INFORMATION: Antimicrobial peptide sequences

<400> SEQUENCE: 25

Phe Ala Leu Ala Leu Lys Ala Leu Lys Lys Leu Lys Lys Ala Leu Lys
1               5                   10                  15

Lys Ala Leu

<210> SEQ ID NO 26
<211> LENGTH: 17
<212> TYPE: PRT
<213> ORGANISM: Artificial Sequence
<220> FEATURE:
<223> OTHER INFORMATION: Antimicrobial peptide sequence

<400> SEQUENCE: 26

Phe Ala Lys Lys Leu Ala Lys Leu Ala Lys Lys Leu Ala Lys Leu Ala
1               5                   10                  15

Leu

<210> SEQ ID NO 27
<211> LENGTH: 13

<212> TYPE: PRT
<213> ORGANISM: Artificial Sequence
<220> FEATURE:
<223> OTHER INFORMATION: Antimicrobial peptide sequences

<400> SEQUENCE: 27

Phe Ala Lys Leu Leu Ala Lys Leu Ala Lys Lys Leu Leu
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Antimicrobial peptide sequences

<400> SEQUENCE: 28

Phe Ala Lys Lys Leu Ala Lys Leu Ala Leu Lys Leu Ala Lys Leu
1               5                   10                  15

<210> SEQ ID NO 29
<211> LENGTH: 10
<212> TYPE: PRT
<213> ORGANISM: Artificial Sequence
<220> FEATURE:
<223> OTHER INFORMATION: Antimicrobial peptide sequences

<400> SEQUENCE: 29

Phe Ala Lys Lys Leu Ala Lys Lys Leu Leu
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Antimicrobial peptide sequence

<400> SEQUENCE: 30

Phe Ala Lys Leu Leu Ala Lys Leu Ala Lys Lys Val Leu
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 31

Lys Tyr Lys Lys Ala Leu Lys Lys Leu Ala Lys Leu Leu
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Antimicrobial peptide sequences

<400> SEQUENCE: 32

Phe Ala Leu Leu Lys Ala Leu Leu Lys Lys Ala Leu
1               5                   10

<210> SEQ ID NO 33
<211> LENGTH: 14
<212> TYPE: PRT

<213> ORGANISM: Artificial Sequence
<220> FEATURE:
<223> OTHER INFORMATION: Antimicrobial peptide sequence

<400> SEQUENCE: 33

Lys Arg Leu Phe Lys Lys Leu Lys Phe Ser Leu Arg Lys Tyr
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 34

Lys Arg Leu Phe Lys Lys Leu Leu Phe Ser Leu Arg Lys Tyr
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 35

Leu Leu Leu Phe Leu Leu Lys Lys Arg Lys Lys Arg Lys Tyr
1               5                   10

<210> SEQ ID NO 36
<211> LENGTH: 36
<212> TYPE: PRT
<213> ORGANISM: Hyalophora cecropia

<400> SEQUENCE: 36

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
            20                  25                  30

Gln Ile Ala Lys
        35

<210> SEQ ID NO 37
<211> LENGTH: 23
<212> TYPE: PRT
<213> ORGANISM: Xenopus sp.

<400> SEQUENCE: 37

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 38
<211> LENGTH: 22
<212> TYPE: PRT
<213> ORGANISM: Xenopus sp.

<400> SEQUENCE: 38

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 39
<211> LENGTH: 12
<212> TYPE: PRT
<213> ORGANISM: Bos taurus

<400> SEQUENCE: 39

Arg Leu Cys Arg Ile Val Val Ile Arg Val Cys Arg
1               5                   10

<210> SEQ ID NO 40
<211> LENGTH: 13
<212> TYPE: PRT
<213> ORGANISM: Bos sp.

<400> SEQUENCE: 40

Ile Leu Pro Trp Lys Trp Pro Trp Trp Pro Trp Arg Arg
1               5                   10

<210> SEQ ID NO 41
<211> LENGTH: 24
<212> TYPE: PRT
<213> ORGANISM: Homo sapiens

<400> SEQUENCE: 41

Asp Ser His Ala Lys Arg His His Gly Tyr Lys Arg Lys Phe His Glu
1               5                   10                  15

Lys His His Ser His Arg Gly Tyr
            20

<210> SEQ ID NO 42
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 42

Met Pro Pro Pro Leu Met Gln
1               5

<210> SEQ ID NO 43
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 43

Phe His Glu Asn Trp Pro Ser
1               5

<210> SEQ ID NO 44
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 44

Arg Thr Ala Pro Thr Thr Pro Leu Leu Leu Ser Leu
1               5                   10

<210> SEQ ID NO 45
<211> LENGTH: 12

```
<212> TYPE: PRT
<213> ORGANISM: Artificial Sequence
<220> FEATURE:
<223> OTHER INFORMATION: Pigment binding peptide sequence

<400> SEQUENCE: 45

Trp His Leu Ser Trp Ser Pro Val Pro Leu Pro Thr
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 46

Pro His Ala Arg Leu Val Gly
1               5

<210> SEQ ID NO 47
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 47

Asn Ile Pro Tyr His His Pro
1               5

<210> SEQ ID NO 48
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 48

Thr Thr Met Pro Ala Ile Pro
1               5

<210> SEQ ID NO 49
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 49

His Asn Leu Pro Pro Arg Ser
1               5

<210> SEQ ID NO 50
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 50

Ala His Lys Thr Gln Met Gly Val Arg Gln Pro Ala
1               5                   10

<210> SEQ ID NO 51
<211> LENGTH: 12
<212> TYPE: PRT
```

```
<213> ORGANISM: Artificial Sequence
<220> FEATURE:
<223> OTHER INFORMATION: Pigment binding peptide sequence

<400> SEQUENCE: 51

Ala Asp Asn Val Gln Met Gly Val Ser His Thr Pro
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 52

Ala His Asn Ala Gln Met Gly Val Ser His Pro Pro
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 53

Ala Asp Tyr Val Gly Met Gly Val Ser His Arg Pro
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 54

Ser Val Ser Val Gly Met Lys Pro Ser Pro Arg Pro
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 55

Tyr Pro Asn Thr Ala Leu Val
1               5

<210> SEQ ID NO 56
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 56

Val Ala Thr Arg Ile Val Ser
1               5

<210> SEQ ID NO 57
<211> LENGTH: 12
<212> TYPE: PRT
<213> ORGANISM: Artificial Sequence
```

```
<220> FEATURE:
<223> OTHER INFORMATION: Pigment binding peptide sequences

<400> SEQUENCE: 57

His Ser Leu Lys Asn Ser Met Leu Thr Val Met Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 58

Asn Tyr Pro Thr Gln Ala Pro
1               5

<210> SEQ ID NO 59
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 59

Lys Cys Cys Tyr Ser Val Gly
1               5

<210> SEQ ID NO 60
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 60

Arg His Asp Leu Asn Thr Trp Leu Pro Pro Val Lys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 61

Glu Ile Ser Leu Pro Ala Lys Leu Pro Ser Ala Ser
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 62

Ser Asp Tyr Val Gly Met Arg Pro Ser Pro Arg His
1               5                   10

<210> SEQ ID NO 63
<211> LENGTH: 12
<212> TYPE: PRT
<213> ORGANISM: Artificial Sequence
<220> FEATURE:
```

-continued

<223> OTHER INFORMATION: Pigment binding peptide sequences

<400> SEQUENCE: 63

Ser Asp Tyr Val Gly Met Arg Leu Ser Pro Ser Gln
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 64

Ser Val Ser Val Gly Ile Gln Pro Ser Pro Arg Pro
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 65

Tyr Val Ser Val Gly Ile Lys Pro Ser Pro Arg Pro
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 66

Tyr Val Cys Glu Gly Ile His Pro Cys Pro Arg Pro
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Print Medium-Binding Peptide

<400> SEQUENCE: 67

Ser Ile Leu Pro Tyr Pro Tyr
1               5

<210> SEQ ID NO 68
<211> LENGTH: 7
<212> TYPE: PRT
<213> ORGANISM: Artificial Sequence
<220> FEATURE:
<223> OTHER INFORMATION: Print Medium-Binding Peptide

<400> SEQUENCE: 68

Ser Thr Ala Ser Tyr Thr Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Print Medium-Binding Peptide

```
<400> SEQUENCE: 69

Leu Pro Val Arg Pro Trp Thr
1               5

<210> SEQ ID NO 70
<211> LENGTH: 7
<212> TYPE: PRT
<213> ORGANISM: Artificial Sequence
<220> FEATURE:
<223> OTHER INFORMATION: Print Medium-Binding Peptide

<400> SEQUENCE: 70

Gly Asn Thr Pro Ser Arg Ala
1               5

<210> SEQ ID NO 71
<211> LENGTH: 7
<212> TYPE: PRT
<213> ORGANISM: Artificial Sequence
<220> FEATURE:
<223> OTHER INFORMATION: Print Medium-Binding Peptides

<400> SEQUENCE: 71

His Ala Ile Tyr Pro Arg His
1               5

<210> SEQ ID NO 72
<211> LENGTH: 7
<212> TYPE: PRT
<213> ORGANISM: Artificial Sequence
<220> FEATURE:
<223> OTHER INFORMATION: Print Medium-Binding Peptides

<400> SEQUENCE: 72

Tyr Gln Asp Ser Ala Lys Thr
1               5

<210> SEQ ID NO 73
<211> LENGTH: 7
<212> TYPE: PRT
<213> ORGANISM: Artificial Sequence
<220> FEATURE:
<223> OTHER INFORMATION: Cellulose Binding Peptide

<400> SEQUENCE: 73

Val Pro Arg Val Thr Ser Ile
1               5

<210> SEQ ID NO 74
<211> LENGTH: 7
<212> TYPE: PRT
<213> ORGANISM: Artificial Sequence
<220> FEATURE:
<223> OTHER INFORMATION: Cellulose-Binding Peptide

<400> SEQUENCE: 74

Met Ala Asn His Asn Leu Ser
1               5

<210> SEQ ID NO 75
<211> LENGTH: 7
<212> TYPE: PRT
<213> ORGANISM: Artificial Sequence
<220> FEATURE:
<223> OTHER INFORMATION: Cellulose-Binding Peptide
```

```
<400> SEQUENCE: 75

Phe His Glu Asn Trp Pro Ser
1               5

<210> SEQ ID NO 76
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 76

Thr His Lys Thr Ser Thr Gln Arg Leu Leu Ala Ala
1               5                   10

<210> SEQ ID NO 77
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 77

Lys Cys Cys Tyr Val Asn Val Gly Ser Val Phe Ser
1               5                   10

<210> SEQ ID NO 78
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 78

Ala His Met Gln Phe Arg Thr Ser Leu Thr Pro His
1               5                   10

<210> SEQ ID NO 79
<211> LENGTH: 12
<212> TYPE: PRT
<213> ORGANISM: Artificial sequence
<220> FEATURE:
<223> OTHER INFORMATION: Poly(ethylene terephthalate)-Binding Peptide

<400> SEQUENCE: 79

Gly Thr Ser Asp His Met Ile Met Pro Phe Phe Asn
1               5                   10

<210> SEQ ID NO 80
<211> LENGTH: 7
<212> TYPE: PRT
<213> ORGANISM: Artificial sequence
<220> FEATURE:
<223> OTHER INFORMATION: Skin Binding Peptide Domain

<400> SEQUENCE: 80

Phe Thr Gln Ser Leu Pro Arg
1               5

<210> SEQ ID NO 81
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 81
```

Thr Pro Phe His Ser Pro Glu Asn Ala Pro Gly Ser
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 82

Lys Gln Ala Thr Phe Pro Pro Asn Pro Thr Ala Tyr
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 83

His Gly His Met Val Ser Thr Ser Gln Leu Ser Ile
1               5                   10

<210> SEQ ID NO 84
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 84

Leu Ser Pro Ser Arg Met Lys
1               5

<210> SEQ ID NO 85
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 85

Leu Pro Ile Pro Arg Met Lys
1               5

<210> SEQ ID NO 86
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 86

His Gln Arg Pro Tyr Leu Thr
1               5

<210> SEQ ID NO 87
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 87

```
Phe Pro Pro Leu Leu Arg Leu
1               5

<210> SEQ ID NO 88
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 88

Ala Leu Pro Arg Ile Ala Asn Thr Trp Ser Pro Ser
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 89

Tyr Pro Ser Phe Ser Pro Thr Tyr Arg Pro Ala Phe
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 90

Tyr Pro Ser Phe Ser Pro Thr Tyr Arg Pro Ala Phe
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 91

Ala Leu Pro Arg Ile Ala Asn Thr Trp Ser Pro Ser
1               5                   10

<210> SEQ ID NO 92
<211> LENGTH: 8
<212> TYPE: PRT
<213> ORGANISM: Artificial Sequence
<220> FEATURE:
<223> OTHER INFORMATION: Hair Binding Peptide Domain

<400> SEQUENCE: 92

Leu Glu Ser Thr Pro Lys Met Lys
1               5

<210> SEQ ID NO 93
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 93

Ser Val Ser Val Gly Met Lys Pro Ser Pro Arg Pro
```

<210> SEQ ID NO 94
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 94

Leu Asp Val Glu Ser Tyr Lys Gly Thr Ser Met Pro
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 95

Arg Val Pro Asn Lys Thr Val Thr Val Asp Gly Ala
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 96

Asp Arg His Lys Ser Lys Tyr Ser Ser Thr Lys Ser
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 97

Lys Asn Phe Pro Gln Gln Lys Glu Phe Pro Leu Ser
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 98

Gln Arg Asn Ser Pro Pro Ala Met Ser Arg Arg Asp
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 99

Thr Arg Lys Pro Asn Met Pro His Gly Gln Tyr Leu
1               5                   10

```
<210> SEQ ID NO 100
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 100

Lys Pro Pro His Leu Ala Lys Leu Pro Phe Thr Thr
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 101

Asn Lys Arg Pro Pro Thr Ser His Arg Ile His Ala
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 102

Asn Leu Pro Arg Tyr Gln Pro Pro Cys Lys Pro Leu
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 103

Arg Pro Pro Trp Lys Lys Pro Ile Pro Pro Ser Glu
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 104

Arg Gln Arg Pro Lys Asp His Phe Phe Ser Arg Pro
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (6)..(6)
<223> OTHER INFORMATION: X= T or P
<220> FEATURE:
<221> NAME/KEY: MISC_FEATURE
```

```
<222> LOCATION: (12)..(12)
<223> OTHER INFORMATION: X= E or A

<400> SEQUENCE: 105

Ser Val Pro Asn Lys Xaa Val Thr Val Asp Gly Xaa
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 106

Thr Thr Lys Trp Arg His Arg Ala Pro Val Ser Pro
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 107

Trp Leu Gly Lys Asn Arg Ile Lys Pro Arg Ala Ser
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 108

Ser Asn Phe Lys Thr Pro Leu Pro Leu Thr Gln Ser
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 109

Lys Glu Leu Gln Thr Arg Asn Val Val Gln Arg Glu
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 110

Gly Met Pro Ala Met His Trp Ile His Pro Phe Ala
1               5                   10

<210> SEQ ID NO 111
<211> LENGTH: 12
<212> TYPE: PRT
<213> ORGANISM: Artificial Sequence
<220> FEATURE:
```

<223> OTHER INFORMATION: Hair Binding Peptide Domain

<400> SEQUENCE: 111

Thr Pro Thr Ala Asn Gln Phe Thr Gln Ser Val Pro
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 112

Ala Ala Gly Leu Ser Gln Lys His Glu Arg Asn Arg
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 113

Glu Thr Val His Gln Thr Pro Leu Ser Asp Arg Pro
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 114

Leu Pro Ala Leu His Ile Gln Arg His Pro Arg Met
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 115

Gln Pro Ser His Ser Gln Ser His Asn Leu Arg Ser
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 116

Arg Gly Ser Gln Lys Ser Lys Pro Pro Arg Pro Pro
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Hair Binding Peptide Domain

```
<400> SEQUENCE: 117

Thr His Thr Gln Lys Thr Pro Leu Leu Tyr Tyr His
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 118

Thr Lys Gly Ser Ser Gln Ala Ile Leu Lys Ser Thr
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 119

Asp Leu His Thr Val Tyr His
1               5

<210> SEQ ID NO 120
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 120

His Ile Lys Pro Pro Thr Arg
1               5

<210> SEQ ID NO 121
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 121

His Pro Val Trp Pro Ala Ile
1               5

<210> SEQ ID NO 122
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 122

Met Pro Leu Tyr Tyr Leu Gln
1               5

<210> SEQ ID NO 123
<211> LENGTH: 26
<212> TYPE: PRT
<213> ORGANISM: Artificial Sequence
<220> FEATURE:
<223> OTHER INFORMATION: Hair Binding Peptide Domain
```

```
<400> SEQUENCE: 123

His Leu Thr Val Pro Trp Arg Gly Gly Gly Ser Ala Val Pro Phe Tyr
1               5                   10                  15

Ser His Ser Gln Ile Thr Leu Pro Asn His
            20                  25

<210> SEQ ID NO 124
<211> LENGTH: 41
<212> TYPE: PRT
<213> ORGANISM: Artificial Sequence
<220> FEATURE:
<223> OTHER INFORMATION: Hair Binding Peptide Domain

<400> SEQUENCE: 124

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
        35                  40

<210> SEQ ID NO 125
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 125

Lys His Pro Thr Tyr Arg Gln
1               5

<210> SEQ ID NO 126
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 126

His Pro Met Ser Ala Pro Arg
1               5

<210> SEQ ID NO 127
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 127

Met Pro Lys Tyr Tyr Leu Gln
1               5

<210> SEQ ID NO 128
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 128

Met His Ala His Ser Ile Ala
1               5
```

```
<210> SEQ ID NO 129
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 129

Thr Ala Ala Thr Thr Ser Pro
1               5

<210> SEQ ID NO 130
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 130

Leu Gly Ile Pro Gln Asn Leu
1               5

<210> SEQ ID NO 131
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 131

Ala Lys Pro Ile Ser Gln His Leu Gln Arg Gly Ser
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 132

Ala Pro Pro Thr Pro Ala Ala Ala Ser Ala Thr Thr
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 133

Asp Pro Thr Glu Gly Ala Arg Arg Thr Ile Met Thr
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 134

Glu Gln Ile Ser Gly Ser Leu Val Ala Ala Pro Trp
1               5                   10
```

```
<210> SEQ ID NO 135
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 135

Leu Asp Thr Ser Phe Pro Pro Val Pro Phe His Ala
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Hair Binding Peptide Domain

<400> SEQUENCE: 136

Leu Pro Arg Ile Ala Asn Thr Trp Ser Pro Ser
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 137

Arg Thr Asn Ala Ala Asp His Pro Ala Ala Val Thr
1               5                   10

<210> SEQ ID NO 138
<211> LENGTH: 12
<212> TYPE: PRT
<213> ORGANISM: Artificial Sequence
<220> FEATURE:
<223> OTHER INFORMATION: HairBinding Peptide Domain

<400> SEQUENCE: 138

Ser Leu Asn Trp Val Thr Ile Pro Gly Pro Lys Ile
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 139

Thr Asp Met Gln Ala Pro Thr Lys Ser Tyr Ser Asn
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 140

Thr Ile Met Thr Lys Ser Pro Ser Leu Ser Cys Gly
1               5                   10

<210> SEQ ID NO 141
```

```
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 141

Thr Pro Ala Leu Asp Gly Leu Arg Gln Pro Leu Arg
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 142

Thr Tyr Pro Ala Ser Arg Leu Pro Leu Leu Ala Pro
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 143

Thr Tyr Pro Ala Ser Arg Leu Pro Leu Leu Ala Pro
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 144

Thr Asp Pro Thr Pro Phe Ser Ile Ser Pro Glu Arg
1               5                   10

<210> SEQ ID NO 145
<211> LENGTH: 20
<212> TYPE: PRT
<213> ORGANISM: Artificial Sequence
<220> FEATURE:
<223> OTHER INFORMATION: Hair Binding Peptide Domain

<400> SEQUENCE: 145

Cys Ala Ala Gly Cys Cys Thr Cys Ala Gly Cys Gly Ala Cys Cys Gly
1               5                   10                  15

Ala Ala Thr Ala
            20

<210> SEQ ID NO 146
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 146

Trp His Asp Lys Pro Gln Asn Ser Ser Lys Ser Thr
1               5                   10
```

```
<210> SEQ ID NO 147
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 147

Asn Glu Val Pro Ala Arg Asn Ala Pro Trp Leu Val
1               5                   10

<210> SEQ ID NO 148
<211> LENGTH: 13
<212> TYPE: PRT
<213> ORGANISM: Artificial Sequence
<220> FEATURE:
<223> OTHER INFORMATION: Hair Binding Peptide Domain

<400> SEQUENCE: 148

Asn Ser Pro Gly Tyr Gln Ala Asp Ser Val Ala Ile Gly
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 149

Thr Gln Asp Ser Ala Gln Lys Ser Pro Ser Pro Leu
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 150

Thr Pro Pro Glu Leu Leu His Gly Asp Pro Arg Ser
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 151

Thr Pro Pro Thr Asn Val Leu Met Leu Ala Thr Lys
1               5                   10

<210> SEQ ID NO 152
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 152

Asn Thr Ser Gln Leu Ser Thr
1               5
```

```
<210> SEQ ID NO 153
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 153

Asn Thr Pro Lys Glu Asn Trp
1               5

<210> SEQ ID NO 154
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 154

Asn Thr Pro Ala Ser Asn Arg
1               5

<210> SEQ ID NO 155
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 155

Pro Arg Gly Met Leu Ser Thr
1               5

<210> SEQ ID NO 156
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 156

Pro Pro Thr Tyr Leu Ser Thr
1               5

<210> SEQ ID NO 157
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 157

Thr Ile Pro Thr His Arg Gln His Asp Tyr Arg Ser
1               5                   10

<210> SEQ ID NO 158
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 158

Thr Pro Pro Thr His Arg Leu
1               5

<210> SEQ ID NO 159
```

```
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 159

Leu Pro Thr Met Ser Thr Pro
1               5

<210> SEQ ID NO 160
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 160

Leu Gly Thr Asn Ser Thr Pro
1               5

<210> SEQ ID NO 161
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 161

Thr Pro Leu Thr Gly Ser Thr Asn Leu Leu Ser Ser
1               5                   10

<210> SEQ ID NO 162
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 162

Thr Pro Leu Thr Lys Glu Thr
1               5

<210> SEQ ID NO 163
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 163

Gln Gln Ser His Asn Pro Pro
1               5

<210> SEQ ID NO 164
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 164

Thr Gln Pro His Asn Pro Pro
1               5

<210> SEQ ID NO 165
<211> LENGTH: 12
```

```
<212> TYPE: PRT
<213> ORGANISM: Artificial Sequence
<220> FEATURE:
<223> OTHER INFORMATION: Hair Binding Peptide Domain

<400> SEQUENCE: 165

Ser Thr Asn Leu Leu Arg Thr Ser Thr Val His Pro
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 166

His Thr Gln Pro Ser Tyr Ser Ser Thr Asn Leu Phe
1               5                   10

<210> SEQ ID NO 167
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 167

Ser Leu Leu Ser Ser His Ala
1               5

<210> SEQ ID NO 168
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 168

Gln Gln Ser Ser Ile Ser Leu Ser Ser His Ala Val
1               5                   10

<210> SEQ ID NO 169
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 169

Asn Ala Ser Pro Ser Ser Leu
1               5

<210> SEQ ID NO 170
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 170

His Ser Pro Ser Ser Leu Arg
1               5

<210> SEQ ID NO 171
<211> LENGTH: 7
<212> TYPE: PRT
```

```
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (2)..(2)
<223> OTHER INFORMATION: X= H, R or N

<400> SEQUENCE: 171

Lys Xaa Ser His His Thr His
1               5

<210> SEQ ID NO 172
<211> LENGTH: 7
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (2)..(2)
<223> OTHER INFORMATION: X=H or Ror N
<220> FEATURE:
<221> NAME/KEY: MISC_FEATURE
<222> LOCATION: (2)..(2)
<223> OTHER INFORMATION: X= H, R, or N

<400> SEQUENCE: 172

Glu Xaa Ser His His Thr His
1               5

<210> SEQ ID NO 173
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 173

Leu Glu Ser Thr Ser Leu Leu
1               5

<210> SEQ ID NO 174
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 174

Thr Pro Leu Thr Lys Glu Thr
1               5

<210> SEQ ID NO 175
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 175

Lys Gln Ser His Asn Pro Pro
1               5

<210> SEQ ID NO 176
<211> LENGTH: 8
<212> TYPE: PRT
<213> ORGANISM: Artificial Sequence
<220> FEATURE:
```

```
-continued

<223> OTHER INFORMATION: Linker Peptide

<400> SEQUENCE: 176

Leu Glu Ser Gly Asp Glu Val Asp
1               5

<210> SEQ ID NO 177
<211> LENGTH: 37
<212> TYPE: PRT
<213> ORGANISM: Artificial Sequence
<220> FEATURE:
<223> OTHER INFORMATION: Linker peptide

<400> SEQUENCE: 177

Thr Ser Thr Ser Lys Ala Ser Thr Thr Thr Thr Ser Ser Lys Thr Thr
1               5                   10                  15

Thr Thr Ser Ser Lys Thr Thr Thr Thr Thr Ser Lys Thr Ser Thr Thr
                20                  25                  30

Ser Ser Ser Ser Thr
            35

<210> SEQ ID NO 178
<211> LENGTH: 22
<212> TYPE: PRT
<213> ORGANISM: Artificial Sequence
<220> FEATURE:
<223> OTHER INFORMATION: Linker peptide

<400> SEQUENCE: 178

Gly Gln Gly Gly Tyr Gly Gly Leu Gly Ser Gln Gly Ala Gly Arg Gly
1               5                   10                  15

Gly Leu Gly Gly Gln Gly
            20

<210> SEQ ID NO 179
<211> LENGTH: 10
<212> TYPE: PRT
<213> ORGANISM: Artificial Sequence
<220> FEATURE:
<223> OTHER INFORMATION: Linker peptide

<400> SEQUENCE: 179

Gly Pro Gly Gly Tyr Gly Pro Gly Gln Gln
1               5                   10
```